US011427826B2

(12) United States Patent
Rossi et al.

(10) Patent No.: US 11,427,826 B2
(45) Date of Patent: Aug. 30, 2022

(54) RNA APTAMERS AGAINST TRANSFERRIN RECEPTOR (TFR)

(71) Applicants: CITY OF HOPE, Duarte, CA (US); APTERNA LIMITED, London (GB)

(72) Inventors: John J. Rossi, Azusa, CA (US); Sorah Yoon, Pasadena, CA (US); Nagy Habib, London (GB)

(73) Assignees: City of Hopw, Duarte, CA (US); Apterna Limited, London (GB)

( * ) Notice: Subject to any disclaimer, the term of this patent is extended or adjusted under 35 U.S.C. 154(b) by 316 days.

(21) Appl. No.: 16/637,679

(22) PCT Filed: Aug. 10, 2018

(86) PCT No.: PCT/US2018/046343
§ 371 (c)(1),
(2) Date: Feb. 7, 2020

(87) PCT Pub. No.: WO2019/033051
PCT Pub. Date: Feb. 14, 2019

(65) Prior Publication Data
US 2020/0172905 A1 Jun. 4, 2020

Related U.S. Application Data

(60) Provisional application No. 62/671,604, filed on May 15, 2018, provisional application No. 62/544,220, filed on Aug. 11, 2017.

(51) Int. Cl.
*C12N 15/115* (2010.01)
*A61K 47/54* (2017.01)

(52) U.S. Cl.
CPC .......... *C12N 15/115* (2013.01); *A61K 47/549* (2017.08); *C12N 2310/16* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,143,854 A | 9/1992 | Pirrung et al. |
| 5,235,033 A | 8/1993 | Summerton et al. |
| 6,344,321 B1 * | 2/2002 | Rabin ............... A61P 15/00 536/23.1 |
| 7,635,472 B2 | 12/2009 | Kufer et al. |
| 8,586,042 B2 | 11/2013 | Wadhwa et al. |
| 8,591,893 B2 | 11/2013 | Wadhwa et al. |
| 2016/0053265 A1 | 2/2016 | Rossi et al. |
| 2016/0326249 A1 | 11/2016 | Ng et al. |
| 2017/0226515 A1 | 8/2017 | Rossi et al. |
| 2020/0181264 A1 | 6/2020 | Rossi et al. |

FOREIGN PATENT DOCUMENTS

| | | |
|---|---|---|
| WO | WO-96/17958 A1 | 6/1996 |
| WO | WO-00/041474 A2 | 7/2000 |
| WO | WO-00/041474 A3 | 7/2000 |
| WO | WO-2006/022344 A1 | 3/2006 |
| WO | WO-2007/033230 A2 | 3/2007 |
| WO | WO-2007/033230 A3 | 3/2007 |
| WO | WO-2008/119565 A2 | 10/2008 |
| WO | WO-2008/119565 A3 | 10/2008 |
| WO | WO-2008/119566 A2 | 10/2008 |
| WO | WO-2008/119566 A3 | 10/2008 |
| WO | WO-2008/119567 A2 | 10/2008 |
| WO | WO-2008/119567 A3 | 10/2008 |
| WO | WO-2008/119567 A8 | 10/2008 |
| WO | WO-2011/071099 A1 | 6/2011 |
| WO | WO-2013/154735 A1 | 10/2013 |
| WO | WO-2014/122143 A1 | 8/2014 |
| WO | WO-2014/147559 A1 | 9/2014 |
| WO | WO-2014/167022 A1 | 10/2014 |
| WO | WO-2014/170063 A1 | 10/2014 |
| WO | WO-2016/019270 A1 | 2/2016 |
| WO | WO-2016/019270 A8 | 2/2016 |
| WO | WO-2016/061386 A1 | 4/2016 |
| WO | WO-2016/061401 A1 | 4/2016 |
| WO | WO-2016/120325 A1 | 8/2016 |
| WO | WO-2016/127216 A1 | 8/2016 |
| WO | WO-2016/161165 A1 | 10/2016 |
| WO | WO-2017/143150 A1 | 8/2017 |
| WO | WO-2019/033050 A1 | 2/2019 |

OTHER PUBLICATIONS

Altschul, S.F. et al. (Oct. 5, 1990). "Basic local alignment search tool," *J Mol Biol* 215(3):403-410.
Altschul, S.F. et al. (Sep. 1, 1997). "Gapped BLAST and PSI-BLAST: a new generation of protein database search programs," *Nucleic Acids Research* 25(17):3389-3402.
Bayer, AL et al. (Jul. 1998). "Transferrin receptor in T cell activation and transplantation," *J Leukoc Biol* 64:19-24.
Bulman, M.P. et al. (Jul. 1997). "A Missense Mutation in the Hepatocyte Nuclear Factor 4 Alpha Gene in a UK Pedigree With Maturity-Onset Diabetes of the Young," *Diabetologia* 40(7):859-862.
Burmeister, P.E. et al. (Jan. 2005). "Direct in Vitro Selection of a 2'-O-methyl Aptamer to VEGF," *Chem. Biol.* 12(1):25-33.
Chu, T.C. et al. (Jan. 1, 2006). "Aptamer Mediated siRNA Delivery," Nucleic Acids Research 34(10):E73 (pp. 1-6).

(Continued)

*Primary Examiner* — Tracy Vivlemore
(74) *Attorney, Agent, or Firm* — Mintz Levin Cohn Ferris Glovsky and Popeo, P.C.

(57) ABSTRACT

A ribonucleic acid compound is disclosed, the ribonucleic acid compound comprising, or consisting of, an RNA sequence having at least 90% sequence identity to SEQ ID NO: 1, wherein said RNA sequence has a length of 29 nucleotides or fewer, and wherein the RNA sequence is capable of binding to a transferrin receptor (TfR).

21 Claims, 11 Drawing Sheets
Specification includes a Sequence Listing.

(56) References Cited

OTHER PUBLICATIONS

Crichton, R.R. et al. (May 4, 1987). "Iron Transport and Storage," *Eur J Biochem* 164(3):485-506.
Daneman, R. et al. (Jan. 5, 2015). "The Blood-Brain Barrier," Perspect Biol 7(1):a020412.
Daniels T.R. et al. (Nov. 2006, e-published Aug. 10, 2006). "The Transferrin Receptor Part I: Biology and Targeting With Cytotoxic Antibodies for the Treatment of Cancer," *Clin Immunol* 121(2):144-158.
Daniels T.R. et al. (Nov. 2006, e-published Aug. 17, 2006). "The Transferrin Receptor Part II: Targeted Delivery of Therapeutic Agents Into Cancer Cells," *Clin Immunol* 121(2):159-176.
Drescher, D.G. et al. (2009). "Surface Plasmon Resonance (SPR) Analysis of Binding Interactions of Proteins in Inner-Ear Sensory Epithelia," *Methods Mol Biol.* 493:323-343.
Ellington, A.D. et al. (Aug. 30, 1990). "In vitro selection of RNA molecules that bind specific ligands," *Nature* 346(6287):818-822.
Fodor, S.P. et al. (Feb. 15, 1991). "Light-directed, spatially addressable parallel chemical synthesis," *Science* (251):4995:767-773.
Gold L. et al. (2010) "Aptamer-based multiplexed proteomic technology for biomarker discovery," *PLoS ONE* 5(12):e15004).
Hamilton, A.J. et al. (Mar. 2014, Epub Nov. 27, 2013). "The HNF4A R76W Mutation Causes Atypical Dominant Fanconi Syndrome in Addition to a β Cell Phenotype," *J Med Genet.* 51(3):165-169.
Hani, E.H. et al. (Feb. 1998). "A Missense Mutation in Hepatocyte Nuclear factor-4 Alpha, Resulting in a Reduced Transactivation Activity, in Human Late-Onset Non-Insulin-Dependent Diabetes Mellitus," *J Clin Invest.* 101(3):521-526.
Holland, J.P. et al. (Sep. 23, 2012). "Annotating MYC status with 89Zr-transferrin imaging," *Nat Med* 18:1586-1591.
Jin, S. et al. (Jan.-Feb. 2007, e-published Jan. 3, 2007). "Role of Autophagy in Cancer: Management of Metabolic Stress," *Autophagy* 3(1):28-31.
Johnston, M. (Feb. 26, 1998). "Gene chips: Array of hope for understanding gene regulation," *Curr. Biol.* 8(5): R171-R174.
Katoh, K. et al. (Apr. 2013, e-published Jan. 16, 2013). "MAFFT Multiple Sequence Alignment Software Version 7: Improvements in Performance and Usability," *Molecular Biology and Evolution* 30(4):772-780.
Kern, S. et al. (Jul. 1997). Direct Hybridization of Large-Insert Genomic Clones on High-Density Gridded cDNA Filter Arrays, *Biotechniques* 23(1):120-124.
Kuwahara, M. et al. (Apr.-Jun. 2013). "In Vitro Selection of BNA (LNA) Aptamers," *Artif DNA PNA XNA* 4(2):39-48.
Lassmann, T. et al. (Dec. 12, 2005). "Kalign—an accurate and fast multiple sequence alignment algorithm," *BMC Bioinformatics* 6(298).
Lin, Y et al. (1994). "Modified RNA Sequence Pools for in Vitro Selection," *Nucleic Acids Res.* 22(24):5229-5234.
Maasch, C. et al. (Sep. 8, 2008). "Physicochemical Stability of NOX-E36, a 40mer L-RNA (Spiegelmer) for Therapeutic Applications," Nucleic Acids Symp. Ser. (Oxf) 52:61-62.
MacDonald, J. et al. (2017). "Development of a Bifunctional Aptamer Targeting the Transferrin Receptor and Epithelial Cell Adhesion Molecule (EpCAM) for the Treatment of Brain Cancer Metastases," *ACS Chem. Neurosci.* 8:777-784.
Mah, L.Y. et al. (Jan. 1, 2012). "Autophagy and Cancer," *Cold Spring Harb Perspect Biol.* 4(1): a008821.
Marcus-Sakura, C.J. (Aug. 1, 1988). "Techniques for using antisense oligodeoxyribonucleotides to study gene expression," Anal. Biochem. 172(2):289-295.
McNamara, J.O. et al. (Jan. 2008). "Multivalent 4-1BB Binding Aptamers Costimulate CD8+ T Cells and Inhibit Tumor Growth in Mice," *J. Clin. Invest.* 118(1):376-386.
Needleman, S.B. et al. (Mar. 1970). "A general method applicable to the search for similarities in the amino acid sequence of two proteins," *J Mol Biol* 48(3):443-453.
Ni, S. et al (2017). "Chemical Modifications of Nucleic Acid Aptamers for Therapeutic Purposes," Int. J. Mol. Sci. 18:1683.
North, B.J. et al. (2004, Apr. 28, 2004). "Sirtuins: Sir2-related NAD-dependent Protein Deacetylases," *Genome Biol.* 5(5):224.

Notredame, C. et al. (Sep. 8, 2000). "T-Coffee: A Novel Method for Fast and Accurate Multiple Sequence Alignment," *J. Mol. Biol.* 302:.205-217.
Pardridge, W.M. (Apr. 5, 1999). "Vector-mediated Drug Delivery to the Brain," *Adv Drug Delivery Rev.* 36(2-3):299-321.
Pearson, W.R. et al. (Apr. 1988). "Improved tools for biological sequence comparison," *Proc. Nat'l. Acad. Sci. USA* 85(8):2444-2448.
Preyat, N. et al. (May 2013, e-published Jan. 16, 2013). "Sirtuin Deacylases: A Molecular Link Between Metabolism and Immunity," *J. Leukoc. Biol.* 93(5):669-680.
Qian, Z.M. et al. (Dec. 2002). "Targeted drug delivery via the transferrin receptor-mediated endocytosis pathway," *Pharmacol Rev* 54(4):561-587.
Rosenfeldt, M. T. et al. (2009). "The role of autophagy in tumour development and cancer therapy," *Expert Rev Mol Med.* 11:e36.
Ruckman, J. et al. (Aug. 1998). "2'-Fluoropyrimidine RNA-based Aptamers to the 165-amino Acid Form of Vascular Endothelial Growth Factor (VEGF165). Inhibition of Receptor Binding and VEGF-induced Vascular Permeability Through Interactions Requiring the Exon 7-encoded Domain," *J. Biol. Chem.* 273(32):20556-20567.
Satoh, A. et al. (Jul. 28, 2010). "SIRT1 Promotes the Central Adaptive Response to Diet Restriction through Activation of the Dorsomedial and Lateral Nuclei of the Hypothalamus," *J Neurosci.* 30(30): 10220-10232.
Schummer, M. et al. (Dec. 1997). "Inexpensive Handheld Device for the Construction of High-Density Nucleic Acid Arrays," *Biotechniques* 23(6):1087-1092.
Smith, T.F. et al. (1981). "Comparison of Biosequences," *Adv. App. Math* 2:482-489.
Soding, J. (Apr. 1, 2005). "Protein homology detection by HMM-HMM comparison," *Bioinformatics* 21(7):951-960.
Srisawat, C. et al. (Feb. 2002). "RNA affinity tags for purification of RNAs and ribonucleoprotein complexes," *Methods* 26(2):156-161.
Stoltenburg, R. et al. (Oct. 2007). "SELEX-A (R)evolutionary Method to Generate High-Affinity Nucleic Acid Ligands," *Biomol Eng* 24(4):381-403.
Tuerk, C. et al. (Aug. 3, 1990). "Systematic evolution of ligands by exponential enrichment: RNA ligands to bacteriophage T4 DNA polymerase," *Science* 249(4968): 505-510.
Tuerk, C. (1997). "Using the SELEX combinatorial chemistry process to find high affinity nucleic acid ligands to target molecules," *Methods Mol Biol* 67:219-230.
Veedu, R. N. et al. (2009). "Locked nucleic acid nucleoside triphosphates and polymerases: on the way towards evolution of LNAaptamers," *J. Mol. Biosyst.* 5:787-792.
Walker, S.C. et al. (2008). "RNA Affinity Tags for the Rapid Purification and Investigation of RNAs and RNA-Protein Complexes," *Methods Mol Biol.* 488: 23-40.
Weintraub, H.M. et al. (Jan. 1990). "Antisense RNA and DNA," *Sci Am* 262(1):40-46.
Ying, W. (Jan. 1, 2007). "NAD+ and NADH in Brain Functions, Brain Diseases and Brain Aging," *Front Biosci.* 12:1863-1888.2.
Zhou, J. et al. (Mar. 2017, e-published Nov. 3, 2016). "Aptamers as targeted therapeutics: current potential and challenges," *Nat Rev Drug Discov* 16(3):181-202.
Zhou, J. et al. (May 2009, e-published Mar. 21, 2009). "Selection, characterization and application of new RNA HIV gp 120 aptamers for facile delivery of Dicer substrate siRNAs into HIV infected cells," *Nucleic Acids Res.* 37(9):3094-3109.
Zhu, G. et al. (Jun. 17, 2015). "Aptamer-Drug Conjugates," *Bioconjug Chem.* 26(11):2186-2197.
International Search Report dated Dec. 12, 2018, for PCT Application No. PCT/US2018/046343, filed Aug. 10, 2018, 5 pages.
Written Opinion dated Dec. 12, 2018, for PCT Application No. PCT/US2018/046343, filed Aug. 10, 2018, 5 pages.
Ando, K. et al. (Apr. 2014, e-published Jul. 5, 2013). "Mortalin Is a Prognostic Factor of Gastric Cancer With Normal p53 Function," Gastric Cancer 17(2):255-262.
Bagatell, R. et al. (Aug. 2004). "Altered Hsp90 function in cancer: A unique therapeutic opportunity," *Mol Cancer Ther* 3:1021-1030.

(56) References Cited

OTHER PUBLICATIONS

Beaucage, S.L. et al. (Mar. 20, 1992). "Advances in the Synthesis of Oligonucleotides by the Phosphoramidite Approach," *Tetrahedron* 48(12):2223-2311.

Berinstein, N.L. (Apr. 15, 2002). "Carcinoembryonic Antigen as a Target for Therapeutic Anticancer Vaccines: A Review," *J Clin Oncol* 20(8):2197-2207.

Chen, J. et al. (Jan. 2014, Nov. 1, 2013). "Overexpression of Mortalin in Hepatocellular Carcinoma and Its Relationship With Angiogenesis and Epithelial to Mesenchymal Transition," *Int J Oncol* 44(1):247-255.

Chen, X. et al. (Aug. 2011, e-published Jun. 28, 2011). "Expression of Mortalin Detected in Human Liver Cancer by Tissue Microarrays," *Anat Rec* 294(8):1344-1351.

Chen, X. et al. (Oct. 2013, e-published Sep. 29, 2012). "Fusion Protein Linkers: Property, Design and Functionality," *Adv Drug Deliv Rev* 65(10):1357-1369.

Chothia, C. et al. (Aug. 20, 1987). "Canonical Structures for the Hypervariable Regions of Immunoglobulins," *J. Mol. Biol.* 196:901-917.

Concepcion, J. et al. Sep. 2009). "Label-free Detection of Biomolecular Interactions Using BioLayer Interferometry for Kinetic Characterization," *Comb Chem High Throughput Screen* 12(8)791-800.

Conte, M. et al.(Oct. 1, 2009, e-published Jul. 17, 2009). "A Mortalin-Like Gene Is Crucial for Planarian Stem Cell Viability," *Dev Biol.* 334(1):109-118.

Dores-Silva, P.R. et al. (Jan. 23, 2015). "Human Mitochondrial Hsp70 (Mortalin): Shedding Light on ATPase Activity, Interaction with Adenosine Nucleotides, Solution Structure and Domain Organization," *PLoS One* 10(1):e0117170.

Dundas, S.R. et al. (2005). "Mortalin Is Over-Expressed by Colorectal Adenocarcinomas and Correlates With Poor Survival," *J Pathol* 205(1):74-81.

Eaton, B.E. et al. (Jun. 1997). "Post-SELEX combinatorial optimization of aptamers," Biorg Med Chem 5(6):1087-1986.

Gilboa, E. et al. (Mar. 1, 2013). "Use of oligonucleotide aptamer ligands to modulate the function of immune receptors," *Clin Cancer Res* 19(5):1054-1062.

Gong, H. et al. (2016). "Simple Method to Prepare Oligonucleotide-Conjugated Antibodies and Its Application in Multiplex Protein Detection in Single Cells," *Bioconjugate Chem.* 27(1): 217-225.

Hearty, S. et al. (2012). "Measuring Antibody-Antigen Binding Kinetics Using Surface Plasmon Resonance," *Methods Mol Biol* 907:411-442.

Herrmann, A. et al. (Jul. 1, 2014). "CTLA4 aptamer delivers STAT3 siRNA to tumor-associated and malignant T cells," *J Clin Invest* 124(7):2977-2987.

Jerabek-Willemsen, M. et al. (Aug. 2011). "Molecular Interaction Studies Using Microscale Thermophoresis," *Assay Drug Dev Technol* 9(4):342-353.

Jin, H. et al. (Mar. 9, 2016). "The Clinicopathological Significance of Mortalin Overexpression in Invasive Ductal Carcinoma of Breast," *J Exp Clin Cancer Res* 35:42.

Kaul, S.C. et al. (Apr. 2007, e-published Dec. 22, 2006). "Three Faces of Mortalin: A Housekeeper, Guardian and Killer," *Exp Gerontol* 42(4):263-274.

Kjer-Nielsen, L. et al. (2004, e-published May 10, 2004). "Crystal Structure of the Human T Cell Receptor CD3 Epsilon Gamma Heterodimer Complexed to the Therapeutic mAb OKT3," *PNAS USA* 101(20):7675-7680.

Ku, T-H. et al. (2015). "Nucleic Acid Aptamers: An Emerging Tool for Biotechnology and Biomedical Sensing," *Sensors* 15:16281-16313.

Lad, L. et al., (Apr. 2015, e-published Nov. 25, 2014). "High-throughput Kinetic Screening of Hybridomas to Identify High-Affinity Antibodies Using Bio-Layer Interferometry," *J Biomol Screen* 20(4):498-507.

Liao-Chan, S. et al. (Apr. 20, 2015). "Quantitative Assessment of Antibody Internalization With Novel Monoclonal Antibodies Against Alexa Fluorophores," *PLoS One* 10(4): e0124708.

Lu, W-J. et al. (Jun. 2011, e-published Jan. 14, 2011). "Mortalin-p53 Interaction in Cancer Cells Is Stress Dependent and Constitutes a Selective Target for Cancer Therapy," *Cell Death Differ* 18(6):1046-1056.

MacDonald, J. et al. (2016). "Truncation and Mutation of a Transferrin Receptor Aptamer Enhances Binding Affinity," *Nucleic Acid Therapeutics* 26(8):348-354.

Mizukoshi, E. et al. (Oct. 1999). "Fibroblast Growth factor-1 Interacts With the Glucose-Regulated Protein GRP75/mortalin," *Biochem. J.* 343 Pt2(2):461-466.

Nath, N. et al. (Apr. 2016, e-published Feb. 3, 2016). "Homogeneous Plate Based Antibody Internalization Assay Using pH Sensor Fluorescent Dye," *J Immunol Methods* 431:11-21.

Nwe, K. et al. (Jun. 2009) "Growing Applications of "Click Chemistry" for Bioconjugation in Contemporary Biomedical Research," *Cancer Biother Radiopharm* 24(3):289-302.

Oelkrug, C. et al. (Jan. 2015, e-published Oct. 29, 2014). "Antibody- and aptamer-strategies for GvHD prevention," *J Cell Mol Med* 19(1):11-20.

Pilzer, D. et al. (Sep. 2005, e-published Aug. 9, 2005). "Mortalin/GRP75 Promotes Release of Membrane Vesicles From Immune Attacked Cells and Protection From Complement-Mediated Lysis," *Int Immunol* 17:1239-1248.

Prodeus, A. et al. (Apr. 28, 2015,). "Targeting the PD-1/PD-L1 Immune Evasion Axis With DNA Aptamers as a Novel Therapeutic Strategy for the Treatment of Disseminated Cancers," *Mol Ther Nucleic Acids* 4:e237.

Retter, I. et al. (Jan. 1, 2005). "VBASE2, an Integrative V Gene Database," *Nucl. Acids Res.* 33 (suppl 1):D671-D674.

Rich, R.L. et al. (Feb. 1, 2008, e-published Aug. 19, 2007). "Extracting Kinetic Rate Constants From Surface Plasmon Resonance Array Systems," *Anal Biochem.* 373(1):112-120.

Roy, S. et al. (Nov. 18, 2013). "Synthesis of DNA/RNA and Their Analogs via Phosphoramidite and H-phosphonate Chemistries," *Molecules* 18:14268-14284.

Rozenberg, P. et al. (Jul. 15, 2013, e-published Feb. 12, 2013). "Elevated Levels of Mitochondrial Mortalin and Cytosolic HSP70 in Blood as Risk Factors in Patients With Colorectal Cancer," *Int J Cancer* 133(2):514-518.

Ryu, J. et al. (Sep. 5, 2014, e-published Jul. 10, 2014). "Identification and Functional Characterization of Nuclear Mortalin in Human Carcinogenesis," *J Biol Chem* 289(36):24832-24844.

Sane, S. et al. (Mar. 13, 2014). "Ubiquitin-like (UBX)-domain-containing Protein, UBXN2A, Promotes Cell Death by Interfering With the p53-Mortalin Interactions in Colon Cancer Cells," *Cell Death Dis.* 5(3):e1118.

Sane, S. et al. (Mar. 2016, e-published Dec. 4, 2015). "Structural studies of UBXN2A and mortalin interaction and the putative role of silenced UBXN2A in preventing response to chemotherapy," *Cell Stress Chaperones* 21(2):313-326.

Santulli-Marotto, S. et al. (Nov. 1, 2003). "Multivalent RNA aptamers that inhibit CTLA-4 and enhance tumor immunity," *Cancer Res* 63(21):7483-7489.

Satelli, A. et al. (Sep. 2011, e-published Jun. 3, 2011). "Vimentin in cancer and its potential as a molecular target for cancer therapy," *Cell Mol Life Sci* 68(18):3033-3046.

Schroeder, H.W. et al. (Feb. 2010). "Structure and Function of Immunoglobulins," *J Allergy Clin Immunol* 125(202):S41-S52.

Sinha, N.D. et al. (Jun. 11, 1984). "Polymer support oligonucleotide synthesis XVIII: use of beta-cyanoethyl-N,N-dialkylamino-/N-morpholino phosphoramidite of deoxynucleosides for the synthesis of DNA fragments simplifying deprotection and isolation of the final product.," *Nucl Acids Res* 12(11):4539-4557.

Stangl et al. (Jan. 11, 2011, e-published Dec. 27, 2010). "Targeting Membrane Heat-Shock Protein 70 (Hsp70) on Tumors by cmHsp70.1 Antibody," *PNAS U S A* 108(2):733-738.

Tai-Nagara, I. et al. (Jan. 2, 2014, e-published Nov. 15, 2013). "Mortalin and DJ-1 Coordinately Regulate Hematopoietic Stem Cell Function Through the Control of Oxidative Stress," *Blood* 123(1):41-50.

(56) References Cited

OTHER PUBLICATIONS

Wadhwa, R. et al. (Jun. 15, 2006). "Upregulation of mortalin/mthsp70/Grp75 Contributes to Human Carcinogenesis," *Int J Cancer* 118(12):2973-2980.

Wang, C-W. et al. (Sep. 2013, e-published Jun. 19, 2013). "A new nucleic acid-based agent inhibits cytotoxic T lymphocyte-mediated immune disorders," *J Allergy Clin Immunol* 132(3):713-722.

Wheeler, L.A. et al. (Jun. 2011, e-published May 16, 2011). "Inhibition of HIV transmission in human cervicovaginal explants and humanized mice using CD4 aptamer-siRNA chimeras," *J Clin Invest* 121(6):2401-2412.

Wu, P-K. et al. (Oct. 2013, e-published Aug. 19, 2013). "A mortalin/HSPA9-mediated Switch in Tumor-Suppressive Signaling of Raf/MEK/extracellular Signal-Regulated Kinase," *Mol Cell Biol* 33(20):4051-4067.

Yang, L. et al. (Dec. 16, 2011, e-published Sep. 24, 2011). "Crosstalk Between Raf/MEK/ERK and PI3K/AKT in Suppression of Bax Conformational Change by Grp75 Under Glucose Deprivation Conditions," *J Mol Biol* 414(5):654-666.

Yl, X. et al. (Feb. 2008, e-published Oct. 14, 2007). "Association of Mortalin (HSPA9) With Liver Cancer Metastasis and Prediction for Early Tumor Recurrence," *Mol Cell Proteomics* 7(2):315-325.

Yoo, J.Y. et al. (Jul. 2010). "Tumor Suppression by Apoptotic and Anti-Angiogenic Effects of Mortalin-Targeting Adeno-Oncolytic Virus," *J Gene Med* 12(7):586-595.

Yoon, S. et al. (Aug. 21, 2019). "Targeted Delivery of C/EBPα-saRNA by RNA Aptamers Shows Anti-tumor Effects in a Mouse Model of Advanced PDAC," *Molecular Therapy: Nucleic Acids* 18:142-154.

Zaritskaya, L. et al. (Jun. 2010). "New Flow Cytometric Assays for Monitoring Cell-Mediated Cytotoxicity," *Expert Rev Vaccines* 9(6):601-616.

Zhang, P. et al. (Oct. 2010). "Combination of an aptamer probe to CD4 and antibodies for multicolored cell phenotyping," *Am J Clin Pathol* 134(4):586-593.

Zhou, J. et al. (Mar. 19, 2015, e-published Mar. 5, 2015). "Cell-specific RNA aptamer against human CCR5 specifically targets HIV-1 susceptible cells and inhibits HIV-1 infectivity," *Chem Biol* 22(3):379-390.

Zhou, Q. et al. (Aug. 28, 2012, e-published Aug. 14, 2012). "Aptamer-containing surfaces for selective capture of CD4 expressing cells," *Langmuir* 28(34):12544-12549.

Extended European Search Report dated Apr. 6, 2021, for EP Patent Application No. 18844104.2, 7 pages.

International Search Report dated Dec. 20, 2018, for PCT Application No. PCT/US2018/046342, filed Aug. 10, 2018, 5 pages.

Written Opinion dated Dec. 20, 2018, for PCT Application No. PCT/US2018/046342, filed Aug. 10, 2018, 9 pages.

\* cited by examiner

| Name | ka (1/Ms) | kd (1/s) | $K^D$ (M) |
|---|---|---|---|
| TR14 S1-3 (22-nt) | 6.30E+06 | 1.38E-04 | 2.20E-11 |

SEQUENCE LISTING

```
<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: TR14 S1-3 (22mer)

<400> SEQUENCE: 1
uuuauucaca uuuuugaauu ga                                          22

<210> SEQ ID NO 2
<211> LENGTH: 87
<212> TYPE: RNA
<213> ORGANISM: Artificial Sequence
<220> FEATURE:
<223> OTHER INFORMATION: TR14 (87mer)

<400> SEQUENCE: 2
gggagacaag aauaaacgcu caaugcguuc acguuuauuc acauuuuuga auugagcaug    60
agcuucgaca ggaggcucac aacaggc                                      87

<210> SEQ ID NO 3
<211> LENGTH: 43
<212> TYPE: RNA
```

```
<213> ORGANISM: Artificial Sequence
<220> FEATURE:
<223> OTHER INFORMATION: TR14 S2 (43mer)

<400> SEQUENCE: 3
ggggcucaau gcguucacgu uuauucacau uuuugaauug agc                43

<210> SEQ ID NO 4
<211> LENGTH: 8
<212> TYPE: RNA
<213> ORGANISM: Artificial Sequence
<220> FEATURE:
<223> OTHER INFORMATION: 8mer loop region

<400> SEQUENCE: 4 acauuuuu                                                        8

<210> SEQ ID NO 5
<211> LENGTH: 16
<212> TYPE: RNA
<213> ORGANISM: Artificial Sequence
<220> FEATURE:
<223> OTHER INFORMATION: 16mer truncation

<400> SEQUENCE: 5
auucacauuu uugaau                                              16

<210> SEQ ID NO 6
<211> LENGTH: 760
<212> TYPE: PRT
<213> ORGANISM: Artificial Sequence
<220> FEATURE:
<223> OTHER INFORMATION: Human transferrin receptor protein 1 isoform 1

<400> SEQUENCE: 6
```

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg

```
            195                 200                 205
Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620
```

```
Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
            725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 7
<211> LENGTH: 21
<212> TYPE: RNA
<213> ORGANISM: Artificial Sequence
<220> FEATURE:
<223> OTHER INFORMATION: SIRT1 saRNA sense

<400> SEQUENCE: 7
auauguccuc cugggaagau u                                          21

<210> SEQ ID NO 8
<211> LENGTH: 21
<212> TYPE: RNA
<213> ORGANISM: Artificial Sequence
<220> FEATURE:
<223> OTHER INFORMATION: SIRT1 saRNA antisense

<400> SEQUENCE: 8
ucuucccagg aggacauauu u                                          21

<210> SEQ ID NO 9
<211> LENGTH: 21
<212> TYPE: RNA
<213> ORGANISM: Artificial Sequence
<220> FEATURE:
<223> OTHER INFORMATION: CEBPA saRNA sense

<400> SEQUENCE: 9
gcggucauug ucacuggucu u                                          21

<210> SEQ ID NO 10
<211> LENGTH: 21
<212> TYPE: RNA
<213> ORGANISM: Artificial Sequence
<220> FEATURE:
<223> OTHER INFORMATION: CEBPA saRNA antisense

<400> SEQUENCE: 10
gaccagugac aaugaccgcu u                                          21

<210> SEQ ID NO 11
<211> LENGTH: 87
```

```
<212> TYPE: RNA
<213> ORGANISM: Artificial Sequence
<220> FEATURE:
<223> OTHER INFORMATION: P19

<400> SEQUENCE: 11
gggagacaag aauaaacgcu caauggcgaa ugcccgccua auagggcguu augacuuguu      60
gaguucgaca ggaggcucac aacaggc                                         87
```

RNA APTAMERS AGAINST TRANSFERRIN RECEPTOR (TFR)

CROSS-REFERENCES TO RELATED APPLICATIONS

This application is the national stage filing under USC 371 of international application PCT/US18/46343, filed Aug. 10, 2018, which claims priority to U.S. Provisional Application No. 62/544,220, filed Aug. 11, 2017, and U.S. Provisional Application No. 62/671,604, filed May 15, 2018, which are hereby incorporated by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-714N01US_Sequence_Listing_ST25.txt, created Feb. 6, 2020, 8,894 bytes, machine format IBM-PC, MS Windows operating system, is hereby incorporated by reference.

FIELD OF THE INVENTION

The present invention relates to nucleic acid compounds, in particular ribonucleic acid compounds, capable of binding the transferrin receptor and compositions and methods using the same.

BACKGROUND

The transferrin receptor (TfR) is a membrane glycoprotein expressed on the cellular surface which mediates cellular uptake of iron from the plasma glycoprotein transferrin. Transferrin binds to iron to create transferrin-iron complexes (Crichton & Charloteaux-Wauters, *Eur J Biochem* 1987; 164(3):485-506). These complexes bind to TfR and bound transferrin is internalised into cells via receptor-mediated endocytosis (Qian Z M et al., *Pharmacol Rev.* 2002, 54(4): 561-587). Transferrin and iron are subsequently released in endosomes.

TfR is typically expressed at low levels on a range of normal cells and is highly expressed on cells with high proliferation rates, including activated immune cells (Bayer A L et al., *J Leukoc Biol* 1998 64: 19-24; Holland J P et al., *Nat Med* 2012 18: 1586-1591) and cancer cells (Daniels T R et al., *Clin Immunol* 2006 121: 144-158; Daniels T R et al., *Clin Immunol* 2006 121: 159-176). Thus, compounds capable of binding to TfR on the surface of TfR-expressing cells and internalising into the cell would be useful for targeted delivery of such compounds.

Aptamers, sometimes described as chemical antibodies, are small single stranded RNA or DNA molecules that bind to their target through shape recognition (Stottenburg R et al., *Biomol Eng.* 2007 October; 24(4):381-403). Aptamers comprise unique three-dimensional structures that are capable of specific molecular recognition of their cognate targets, and they display a number of advantages over antibodies, including their size, production process, increased stability and lack of immunogenicity. Aptamers capable of binding TfR have been described in WO 2016/061386, hereby incorporated by reference in its entirety.

Aptamers that bind TfR could find use in providing targeted delivery of therapeutic payloads to cells throughout the body. However, the treatment of brain disorders is hindered greatly by the presence of the blood-brain barrier (BBB), which restricts the majority of small molecules from entering the brain. Macdonald et al (*ACS Chem. Neurosci.* 2017, 8, 777-784) describe a bifunctional aptamer with the ability to bind to TfR and cross the BBB.

Further mechanisms for targeted therapeutic delivery are needed.

SUMMARY OF THE INVENTION

The present invention provides nucleic acid compounds, preferably ribonucleic acid compounds or deoxyribonucleic acid compounds, comprising a RNA/DNA sequence which is capable of binding to a transferrin receptor (TfR). The nucleic acid compounds have a length of 29 nucleotides or fewer.

In one aspect of the present invention, there is provided a ribonucleic acid compound comprising, or consisting of, an RNA sequence having at least 90% sequence identity to SEQ ID NO:1, wherein said RNA sequence has a length of 29 nucleotides or fewer. The RNA sequence may preferably be capable of binding to a transferrin receptor (TfR).

In some embodiments, the RNA sequence has a length of 22 nucleotides or fewer. In some embodiments, the RNA sequence is 22 nucleotides in length. In some embodiments, the RNA sequence has 100% sequence identity to SEQ ID NO:1.

In another aspect, the present invention provides a ribonucleic acid compound comprising, or consisting of, an RNA sequence having at least 90% sequence identity to SEQ ID NO:5, wherein said RNA sequence has a length of 29 nucleotides or fewer, and wherein the RNA sequence is capable of binding to a transferrin receptor (TfR).

In some embodiments, the RNA sequence is 16 nucleotides in length. In some embodiments, the RNA sequence has 100% sequence identity to SEQ ID NO:5.

In another aspect, the compound is a deoxyribonucleic acid compound comprising, or consisting of, a DNA sequence comprising SEQ ID NO:1 or SEQ ID NO:5 in which one or some or all of the ribonucleotides in SEQ ID NO:1 or SEQ ID NO:5 are substituted for their equivalent deoxyribonucleotide residues dAMP, dGMP, dTMP or dCMP, wherein said DNA sequence has a length of 29 nucleotides or fewer, and optionally wherein the DNA sequence is capable of binding to a transferrin receptor (TfR).

In some embodiments, the ribonucleic acid compound or deoxyribonucleic acid compound is capable of binding to TfR on a cell surface. In some embodiments, the ribonucleic acid compound or deoxyribonucleic acid compound is capable of being internalised into a cell. In some embodiments, the ribonucleic acid compound or deoxyribonucleic acid compound is capable of traversing the blood-brain barrier.

In some embodiments, a nucleic acid compound provided herein further comprises a compound moiety attached to the RNA/DNA sequence. In some embodiments, the compound moiety is a therapeutic moiety or an imaging moiety. In some embodiments, the compound moiety is covalently attached to the RNA/DNA sequence.

In some embodiments, the therapeutic moiety is a nucleic acid moiety, a peptide moiety or a small molecule drug moiety. In some embodiments, the therapeutic moiety is an activating nucleic acid moiety or an antisense nucleic acid moiety. In some embodiments, the therapeutic moiety is a miRNA, mRNA, saRNA or siRNA moiety. In some embodiments, the therapeutic moiety is an anticancer therapeutic moiety. In some embodiments, the therapeutic moiety is a C/EBPalpha saRNA moiety, a SIRT1 saRNA moiety, or a HNF saRNA moiety.

In some embodiments, the imaging moiety is a bioluminescent molecule, a photoactive molecule, a metal or a nanoparticle.

Also provided is a pharmaceutical composition comprising a nucleic acid compound according to the present invention. The composition may optionally comprise a pharmaceutically acceptable excipient. In some embodiments, the composition further comprises a therapeutic agent, optionally an anticancer agent.

The present invention also provides a method of delivering a compound moiety into a cell, the method comprising: (i) contacting a cell with a nucleic acid compound according to the present invention; and (ii) allowing said nucleic acid compound to bind to a transferrin receptor on said cell and pass into said cell thereby delivering said compound moiety into said cell.

Also provided is a method of delivering a compound into a cell, the method comprising: (i) contacting a cell with a compound and a nucleic acid compound according to the present invention; and (ii) allowing said ribonucleic acid compound to bind to a transferrin receptor on said cell and pass into said cell thereby delivering said compound into said cell. In some embodiments, the compound is a therapeutic agent or an imaging agent.

In another aspect the present invention provides a nucleic acid compound according to the present invention for use in a method of medical treatment or prophylaxis.

Also provided is the use of a nucleic acid compound according to the present invention in the manufacture of a medicament for treating or preventing a disease or disorder.

Also provided is a method treating or preventing a disease or disorder, the method comprising administering to a subject in need thereof an effective amount of a nucleic acid compound according to the present invention.

In some embodiments, the disease or disorder is cancer. In some embodiments, the method comprises administering an anticancer agent. In some embodiments, the disease or disorder is a metabolic disorder or a neurological disorder.

Also provided is a method of detecting a cell, the method comprising: (i) contacting a cell with a nucleic acid compound according to the present invention, wherein the nucleic acid compound comprises an imaging moiety; (ii) allowing the nucleic acid compound to bind to a transferrin receptor on said cell and pass into said cell; and (iii) detecting said imaging moiety thereby detecting said cell.

Also provided is a method of detecting a cell, the method comprising: (i) contacting a cell with an imaging agent and a nucleic acid compound according to the present invention; (ii) allowing the nucleic acid compound to bind to a transferrin receptor on said cell and allowing said imaging agent to pass into said cell; and (iii) detecting said imaging agent thereby detecting said cell.

The invention includes the combination of the aspects and preferred features described except where such a combination is clearly impermissible or expressly avoided.

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, noncovalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23:1087-1092; Kern (1997) Biotechniques 23:120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "aptamer" as provided herein refers to oligonucleotides (e.g. short oligonucleotides or deoxyribonucleotides), that bind (e.g. with high affinity and specificity) to proteins, peptides, and small molecules. Aptamers typically have defined secondary or tertiary structure owing to their propensity to form complementary base pairs and, thus, are often able to fold into diverse and intricate molecular structures. The three-dimensional structures are essential for aptamer binding affinity and specificity, and specific three-dimensional interactions drives the formation of aptamer-target complexes. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, flexible structure, low immunogenicity, and versatile synthetic accessibility. To date, a variety of anti-cancer agents (e.g. chemotherapy drugs, toxins, and siRNAs) have been successfully delivered to cancer cells in vitro using aptamers.

An "antisense nucleic acid" as referred to herein is a nucleic acid (e.g. DNA or RNA molecule) that is complementary to at least a portion of a specific target nucleic acid (e.g. an mRNA translatable into a protein) and is capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.*, 172:289 (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-30 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when expressed in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a nucleic acid (e.g., ribonucleic acid) and a compound moiety as provided herein can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS, Advances in Chemistry Series, Vol. 198, American Chemical Society, Washington, D.C., 1982. Thus, the nucleic acid acids can be attached to a compound moiety through its backbone. Optionally, the ribonucleic acid includes one or more reactive moieties, e.g., an amino acid reactive moiety, that facilitates the interaction of the ribonucleic acid with the compound moiety.

Useful reactive moieties or functional groups used for conjugate chemistries herein include, for example:
  (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
  (b) hydroxyl groups which can be converted to esters, ethers, aldehydes, etc;
  (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g. phosphines) to form, for example, phosphate diester bonds; and
(n) sulfones, for example, vinyl sulfone.

The reactive functional groups can be chosen such that they do not participate in, or interfere with, the chemical stability of the proteins described herein. By way of example, the nucleic acids can include a vinyl sulfone or other reactive moiety. Optionally, the nucleic acids can include a reactive moiety having the formula S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In some embodiments, about means the specified value.

The terms "protein", "peptide", and "polypeptide" are used interchangeably to denote an amino acid polymer or a set of two or more interacting or bound amino acid polymers. The terms apply to amino acid polymers in which one or more than one amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

For specific proteins described herein (e.g., TfR), the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "TfR" as provided herein includes any of the transferrin receptor (TfR) protein naturally occurring forms, homologs or variants that maintain the activity of TfR (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the TfR protein is the protein as identified by the NCBI sequence reference GI:189458817 (NCBI Reference Sequence: NP_003225.2; SEQ ID NO:6). In embodiments, the TfR protein is the protein as encoded by the nucleotide sequence identified by the NCBI sequence reference GI:189458816 (NCBI Reference Sequence: NM_003234.3). In embodiments, the TfR protein is the protein as encoded by the nucleotide sequence identified by the NCBI sequence reference GI:189458818 (NCBI Reference Sequence: NM_001128148.2). In embodiments, the TfR protein is the protein as identified by the NCBI sequence reference GI:189458817 (NCBI Reference Sequence: NP_003225.2; SEQ ID NO:6), homolog or functional fragment thereof. In embodiments, the TfR protein is the protein as encoded by the nucleotide sequence identified by the NCBI sequence reference GI:189458816 (NCBI Reference Sequence: NM_003234.3), homolog or functional fragment thereof. In embodiments, the TfR protein is the protein as encoded by the nucleotide sequence identified by the NCBI sequence reference GI:189458818 (NCBI Reference Sequence: NM_001128148.2), homolog or functional fragment thereof. In embodiments, the TfR protein is encoded by a nucleic acid sequence corresponding to NCBI Gene ID: 7037.

The term "C/EBPα" or "C/EBPalpha" as provided herein includes any of the CCAAT (cytosine-cytosine-adenosine-adensoine-thymidine)/enhancer-binding protein alpha (C/EBPa) naturally occurring forms, homologs or variants that maintain the transcription factor activity of C/EBPalpha (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the C/EBPalpha protein is the protein as identified by the NCBI sequence reference GI:28872794 (NP_004355.2), GI: 551894998 (NP_001272758.1), GI: 566559992 (NP_001274353.1), or GI: 566559994 (NP_001274364.1), or homolog or functional fragment thereof. In embodiments, the C/EBPalpha protein is encoded by a nucleic acid sequence corresponding to Gene ID:1050.

The term "sirtuin" refers to one or more of the sirtuin class of proteins that possess either mono-ADP-ribosyltransferase or deacetylase activity (including deacetylase, desuccinylase, demalonylase, demyristoylase and depalmitoylase activity). They are dependent on nicotine adenine dinucleotide (NAD) and have been implicated in regulating ageing mechanisms, responses to stress, and disorders such as cancer and diabetes (see e.g. North and Verdin, *Genome Biol.* 2004, 5(5): 224; Preyat and Leo, *J. Leukoc. Biol.* 2013, 93(5): 669-680; and Satoh A et al., *J Neurosci.* 2010, 30(30): 10220-10232, which are all hereby incorporated by reference in their entirety). The human genome encodes seven sirtuin genes: SIRT1 to SIRT7. "SIRT1", "SIRT2", "SIRT3", "SIRT4", "SIRT5", "SIRT6" and "SIRT7" refer to the human Sirtuin genes that encode the Sirt1 to Sirt7 proteins, respectively, including homologs and variants thereof that produce a protein product that maintains the deacetylase activity of one or more of Sirt1-Sirt7 (e.g., within at least 50%, 80%, 90%, 95%, 96%, 97%, 98%, 99% or 100% activity compared to the native protein). The terms "Sirt1", "Sirt2", "Sirt3", "Sirt4", "Sirt5", "Sirt6", and "Sirt7" as provided herein include any naturally occurring forms, homologs or variants that maintain the deacetylase activity of said sirtuin proteins (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In some embodiments, human Sirt1 protein is the protein as identified by the NCBI Reference Sequence: NP_036370.2. In some embodiments, the Sirt1 protein is encoded by a nucleic acid sequence corresponding to Gene ID: 23411. Human Sirt2 may be the protein as identified by GenBank reference AAK51133.1, and may be encoded by a nucleic acid sequence corresponding to Gene ID: 22933. Human Sirt3 may be the protein as identified by GenBank reference AAD40851.1, and may be encoded by a nucleic acid sequence corresponding to Gene ID: 23410. Human Sirt4 may be the protein as identified by NCBI reference NP_036372.1, and may be encoded by a nucleic acid sequence corresponding to Gene ID: 23409. Human Sirt5 may be the protein as identified by GenBank reference AAD40853.1, and may be encoded by a nucleic acid sequence corresponding to Gene ID: 23408. Human Sirt6 may be the protein as identified by GenBank reference CAG33481.1, and may be encoded by a nucleic acid sequence corresponding to Gene ID: 51548. Human Sirt7 may be the protein as identified by NCBI reference NP_057622.1, and may be encoded by a nucleic acid sequence corresponding to Gene ID: 51547.

The term "HNF" refers to one or more hepatocyte nuclear factors. Hepatocyte nuclear factors are a group of transcription factors expressed predominantly in the liver which regulate gene expression. HNF may refer to hepatocyte nuclear factor 4 (HNF4), a nuclear receptor protein expressed mostly in the liver, gut, kidney and pancreatic beta cells. There are two isoforms of human HNF4: HNF4α and HNF4γ expressed by the genes HNF4A and HNF4G, respectively. Human HNF4α and/or HNF4A may be the protein/gene as identified by Uniprot P41235, which also describes at least 7 isoforms of HNF4α that are produced by alternative promoter usage and alternative splicing. Human HNF4γ and/or HNF4G may be the protein/gene as identified by Uniprot Q14541, which also describes two isoforms of HNF4γ produced by alternative splicing. Mutations in or variations of the HNF4A gene have been linked to metabolic disorders including maturity-onset diabetes of the young 1

(MODY1; see e.g. Bulman M P et al., *Diabetologia*. 1997, 40(7):859-62), non-insulin dependent diabetes mellitus (NIDDM; see e.g. Hani E H et al., *J Clin Invest*. 1998, 101(3):521-6), and Fanconi renotubular syndrome 4 with maturity-onset diabetes of the young (FRTS4; see e.g. Hamilton A J et al., *J Med Genet*. 2014, 51(3):165-9). The terms "HNF4α" and "HNF4γ" include any naturally occurring forms, homologs or variants that maintain the activity of HNF4α or HNF4γ (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. The terms "HNF4A" and "HNF4G" include genes as well as homologs and variants thereof that produce a protein product that maintains the activity of one or more of HNF4α and/or HNF4γ (e.g., within at least 50%, 80%, 90%, 95%, 96%, 97%, 98%, 99% or 100% activity compared to the native protein).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

The term "blood-brain barrier" refers to a highly selective semipermeable membrane barrier that separates the circulating blood from the brain and extracellular fluid in the central nervous system. The barrier provides tight regulation of the movement of ions, molecules and cells between the blood and the brain, see e.g. Daneman and Prat, Cold Spring Harb Perspect Biol. 2015; 7(1):a020412. Many therapeutic molecules are generally excluded from transport from blood to brain due to their negligible permeability over the brain capillary endothelial wall.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anticancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomustine, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), anti tumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-I receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the ribonucleic acid compound described herein can be co-administered with or covalently attached to conventional immunotherapeutic agents including, but not limited to, immunostimulants (e.g., Bacillus Calmette-Guerin (BCG), levamisole, interleukin-2, alphainterferon, etc.), monoclonal antibodies (e.g., anti-CD20, anti-HER2, anti-CD52, anti-HLA-DR, anti-PD-1 and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the ribonucleic acid compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is cancer (e.g. liver cancer, pancreatic cancer, pancreatic liver metastases, brain cancer, prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or oesophagus), colorectal cancer, leukemia, acute myeloid leukemia, lymphoma, B cell lymphoma, or multiple myeloma), an infectious disease (e.g., HN infection), an inflammatory disease (e.g., rheumatoid arthritis) or a metabolic disease (e.g., diabetes). In embodiments, the disease is a disease related to (e.g. caused by) an aberrant activity of TfR, TfR phosphorylation, or TfR pathway activity, or pathway activated by TfR. In some embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or oesophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas.

Exemplary cancers that may be treated with a compound, pharmaceutical composition, or method provided herein include pancreatic cancer, liver cancer (e.g. hepatocellular carcinoma), pancreatic liver metastases, lymphoma, sarcoma, bladder cancer, bone cancer, brain cancer (e.g. brain tumor, medulloblastoma, glioblastoma, glioblastoma multiforme), cervical cancer, colon cancer, oesophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, lung cancer (e.g. non-small cell lung carcinoma, squamous cell lung carcinoma, adenocarcinoma, large cell lung carcinoma, small cell lung carcinoma, carcinoid, sarcoma), glioma, neuroblastoma, melanoma, castration-resistant prostate cancer, squamous cell carcinoma (e.g., head, neck, or esophagus), colorectal cancer, acute myeloid leukemia, B cell lymphoma, multiple myeloma, Hodgkin's Disease, Non-Hodgkin's Lymphoma, rhabdomyosarcoma, mesothelioma, endometrial cancer, thrombocytosis, Waldenstrom macroglobulinemia (WM), insulanoma, malignant carcinoid, premalignant skin lesions, testicular cancer, malignant hypercalcemia, adrenal cortical cancer, neoplasms of the endocrine or exocrine pancreas, medullary thyroid cancer, medullary thyroid carcinoma, papillary thyroid cancer, Paget's Disease of the Nipple, Phyllodes Tumors, Lobular Carcinoma, Ductal Carcinoma, cancer of the pancreatic stellate cells, or cancer of the hepatic stellate cells. Additional examples include cancer of the endocrine system, brain, breast, bone, cervix, colon, head & neck, oesophagus, liver, kidney, lung, non-small cell lung, ovary, stomach, mouth, skin, uterus, endometrium, pancreas, thyroid, bladder, prostate, testicle or genitourinary tract.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairycell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HN infection associated disease)) is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

Ribonucleic Acid Compounds

The present invention provides nucleic acid compounds that are inter alia capable of binding a transferrin receptor (TfR). In preferred embodiments, the TfR is on a cell and, in some cases, the nucleic acid compounds are internalised into the cell.

TfR is expressed at low levels on normal cells. Cells with high-proliferation rates, such as activated immune cells and cancers, present upregulated expression of TfR. The nucleic acid compounds of the present invention thus provide a mechanism to target a broad variety of cells via TfR binding.

In various embodiments, the nucleic acid compounds provided herein comprise a payload, such as a therapeutic or diagnostic molecule, and thus facilitate targeted delivery of the payload to TfR-expressing cells. The nucleic acid compounds and the payload may be internalised into TfR-expressing cells, thus providing an efficient mechanism for targeted intracellular delivery.

WO 2016/061386 describes ribonucleic acid compounds that are capable of binding TfR. The ribonucleic acid compounds in WO 2016/061386 comprise RNA sequences having at least 30 nucleotides and are exemplified by compounds comprising RNA sequences that are 87 or 43 nucleotides in length.

The three-dimensional structure of a nucleic acid compound, e.g. an aptamer, is essential for determining binding affinity and specificity. Thus, one cannot truncate a nucleic acid compound with the absolute expectation that it will retain its ability to bind the same target. Predicting functional truncated aptamer sequences is not a trivial exercise. Nevertheless, the inventors have found that specific, shorter nucleic acid sequences of 29 nucleotides or fewer, as provided herein, unexpectedly retain the ability to bind TfR and remain able to be internalised along with a payload into TfR-expressing cells.

In addition, thanks to their reduced size, the nucleic acid compounds described herein are capable of crossing the blood-brain barrier (BBB) and delivering therapeutic or diagnostic payloads to TfR-expressing cell targets in the brain.

Thus, the nucleic acid compounds of the present invention provide highly specific and efficient means for targeted delivery of payloads to a range of cell types in multiple animal species, as shown herein. The present invention also provides a valuable mechanism to overcome the almost impermeable, highly-selective and well-coordinated BBB and achieve delivery of therapeutic and imaging agents to the brain.

In some aspects, the present invention provides a nucleic acid compound comprising, or consisting of, an RNA sequence having at least 80% sequence identity to SEQ ID NO:1, and wherein the RNA sequence has a length of 29 nucleotides or fewer. In any embodiment provided herein, the nucleic acid compound may be a ribonucleic acid compound.

In some embodiments the RNA sequence has at least 85%, at least 87%, at least 90%, at least 91%, at least 92%, at least 93%, at least 94%, at least 95%, at least 96%, at least 97%, at least 98% or at least 99% sequence identity to SEQ ID NO:1. In some embodiments, the RNA sequence has at least 90% sequence identity to SEQ ID NO:1. In some embodiments the RNA sequence has 80%, 85%, 87%, 90%, 91%, 92%, 93%, 94%, 95%, 96%, 97%, 98%, 99% or 100% sequence identity to SEQ ID NO:1. In some embodiments, the RNA sequence has 100% sequence identity to SEQ ID NO:1. In some embodiments, the RNA sequence consists of SEQ ID NO:1. In some embodiments, the RNA sequence is capable of binding to a transferrin receptor (TfR). In some embodiments, the RNA sequence binds to a transferrin receptor (TfR). In some embodiments, the TfR is on a cell surface. In some embodiments, the nucleic acid compound is capable of being internalised into a cell. In some cases, the cell is a TfR-expressing cell.

In some cases the RNA sequence has at least 80% sequence identity to a nucleic acid that hybridises to SEQ ID NO:1. In some cases the RNA sequence has at least 85%, at least 87%, at least 90%, at least 91%, at least 92%, at least 93%, at least 94%, at least 95%, at least 96%, at least 97%, at least 98%, at least 99%, or at least 100% sequence identity to a nucleic acid that hybridises to SEQ ID NO:1.

In some aspects, the present invention provides a nucleic acid compound, e.g. ribonucleic acid compound, comprising or consisting of an RNA sequence having at least 80% sequence identity to SEQ ID NO:5, and wherein the RNA sequence has a length of 29 nucleotides or fewer. In some embodiments the RNA sequence has at least 85%, at least 87%, at least 90%, at least 91%, at least 92%, at least 93%, at least 94%, at least 95%, at least 96%, at least 97%, at least 98% or at least 99% sequence identity to SEQ ID NO:5. In some embodiments, the RNA sequence has at least 90% sequence identity to SEQ ID NO:5. In some embodiments the RNA sequence has 80%, 85%, 87%, 90%, 91%, 92%, 93%, 94%, 95%, 96%, 97%, 98%, 99% or 100% sequence identity to SEQ ID NO:5. In some embodiments, the RNA sequence has 100% sequence identity to SEQ ID NO:5. In some embodiments, the RNA sequence consists of SEQ ID NO:5. In some embodiments, the RNA sequence is capable of binding to a transferrin receptor (TfR). In some embodiments, the RNA sequence binds to a transferrin receptor (TfR). In some embodiments, the TfR is on a cell surface. In some embodiments, the nucleic acid compound is capable of being internalised into a cell. In some cases, the cell is a TfR-expressing cell.

In some cases the RNA sequence has at least 80% sequence identity to a nucleic acid that hybridises to SEQ ID NO:5. In some cases the RNA sequence has at least 85%, at least 87%, at least 90%, at least 91%, at least 92%, at least 93%, at least 94%, at least 95%, at least 96%, at least 97%, at least 98%, at least 99%, or at least 100% sequence identity to a nucleic acid that hybridises to SEQ ID NO:5.

In some embodiments an RNA sequence provided herein has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer. In some cases the RNA sequence has a length of 22 nucleotides or fewer. In some embodiments the RNA sequence is between 16 and 29 nucleotides in length. In some embodiments the RNA sequence is between 16 and 22 nucleotides in length.

In some embodiments the RNA sequence is 16 nucleotides in length. In some embodiments the RNA sequence is 17 nucleotides in length. In some embodiments the RNA sequence is 18 nucleotides in length. In some embodiments the RNA sequence is 19 nucleotides in length. In some embodiments the RNA sequence is 20 nucleotides in length. In some embodiments the RNA sequence is 21 nucleotides in length. In some embodiments the RNA sequence is 22 nucleotides in length. In some embodiments the RNA sequence is 23 nucleotides in length. In some embodiments the RNA sequence is 24 nucleotides in length. In some embodiments the RNA sequence is 25 nucleotides in length. In some embodiments the RNA sequence is 26 nucleotides in length. In some embodiments the RNA sequence is 27 nucleotides in length. In some embodiments the RNA sequence is 28 nucleotides in length. In some embodiments the RNA sequence is 29 nucleotides in length.

In some cases, the RNA sequence has at least 80% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 85% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 87% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 90% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 91% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 92% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 93% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 94% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 95% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 96% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 97% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 98% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 99% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some cases, the RNA sequence has at least 100% sequence identity to SEQ ID NO:1 or SEQ ID NO:5 and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer.

In some embodiments, an RNA sequence provided herein comprises or consists of SEQ ID NO:1 and further comprises 1, 2, 3, 4 or more nucleotide modifications to SEQ ID NO:1. Such modifications may be nucleotide additions, substitutions, and/or deletions.

In some cases, an RNA sequence provided herein differs by 1, 2, 3, or 4 nucleotides compared to SEQ ID NO:1.

In some embodiments, an RNA sequence comprises SEQ ID NO:1 wherein one or more of positions 1, 2, 3, 20, 21 and/or 22 are substituted for alternative nucleic acid residues, for example AMP, GMP, UMP, CMP, dAMP, dGMP, dTMP, and/or dCMP. That is, in some embodiments, the RNA sequence comprises SEQ ID NO:5 and 3 additional nucleotides at each of the 5' end and 3' end.

In some embodiments, the RNA sequence comprises or consists of SEQ ID NO:5 and further comprises 1, 2, 3, 4 or more nucleotide modifications to SEQ ID NO:5. Such modifications may be nucleotide additions, substitutions, and/or deletions.

In some cases, an RNA sequence provided herein differs by 1, 2, 3, or 4 nucleotides compared to SEQ ID NO:5.

Nucleotide positions 4 to 8 of SEQ ID NO:1 are predicted to form base pairing with nucleotide positions 15 to 19. Nucleotide positions 1 to 5 of SEQ ID NO:5 are predicted to form base pairing with nucleotide positions 12 to 16. In some embodiments, an RNA sequence comprises SEQ ID NO:1, wherein nucleotides at any i.e. one or more of positions 4 to 8 and/or 15 to 19 are substituted with nucleotide residues that result in non-canonical base pairing. In some embodiments, an RNA sequence comprises SEQ ID NO:5, wherein nucleotides at any i.e. one or more of positions 1 to 5 and/or 12 to 16 are substituted with nucleotide residues that result in non-canonical base pairing. For example, A or U/T may be replaced with C or G and vice versa. In some cases, an U-A pairing may be replaced with U-G.

Any RNA sequence as described herein may further comprise additional nucleotides. Additional nucleotides may be added onto the 5' end, the 3' end, or both the 5' and 3' ends of the RNA sequence. In some embodiments, an RNA sequence comprising SEQ ID NO:1 or SEQ ID NO:5 as described herein comprises a total of 1, 2, 3, 4, 5, 6, 7, 8, 9, 10, 11, 12, 13 or more additional nucleotides. Where an RNA sequence comprises SEQ ID NO:1, the RNA sequence may comprise a total of 7 or fewer additional nucleotides. Where an RNA sequence comprises SEQ ID NO:5, the RNA sequence may comprise a total of 13 or fewer additional nucleotides. In some embodiments, the RNA sequence is capable of binding to a transferrin receptor (TfR). In some embodiments, the RNA sequence binds to a transferrin receptor (TfR). In some embodiments, the TfR is on a cell surface. In some embodiments, the nucleic acid compound is capable of being internalised into a cell. In some cases, the cell is a TfR-expressing cell.

In some embodiments, the RNA sequence comprises or consists of SEQ ID NO:1 or SEQ ID NO:5, further comprises nucleotide modifications and/or additional nucleotides as described herein, and has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer. In some embodiments, the RNA sequence is capable of binding to a transferrin receptor (TfR). In some embodiments, the RNA sequence binds to a transferrin receptor (TfR). In some embodiments, the TfR is on a cell surface. In some embodiments, the nucleic acid compound is capable of being internalised into a cell. In some cases, the cell is a TfR-expressing cell.

A nucleic acid compound provided herein may comprise SEQ ID NO:4. In some embodiments, an RNA sequence provided herein comprises SEQ ID NO:4.

In some aspects, the present invention provides a nucleic acid compound comprising an RNA sequence, the RNA sequence comprising SEQ ID NO:4, and wherein the RNA sequence has a length of 29 nucleotides or fewer, 28 nucleotides or fewer, 27 nucleotides or fewer, 26 nucleotides or fewer, 25 nucleotides or fewer, 24 nucleotides or fewer, 23 nucleotides or fewer, 22 nucleotides or fewer, 21 nucleotides or fewer, 20 nucleotides or fewer, 19 nucleotides or fewer, 18 nucleotides or fewer, 17 nucleotides or fewer, or 16 nucleotides or fewer. In some embodiments, the RNA sequence is capable of binding to a transferrin receptor (TfR). In some embodiments, the RNA sequence binds to a transferrin receptor (TfR). In some embodiments, the TfR is on a cell surface. In some embodiments, the nucleic acid compound is capable of being internalised into a cell. In some cases, the cell is a TfR-expressing cell.

In some cases, a nucleic acid provided herein comprises an RNA sequence comprising SEQ ID NO:4. In some cases, said RNA sequence is 10 to 29 nucleotides in length. In some embodiments, the nucleic acid comprises an RNA sequence, said RNA sequence comprising SEQ ID NO:4 and having a length of 10 to 29 nucleotides, and wherein said nucleic acid binds to a transferrin receptor (TfR). Preferably, the RNA sequence has a length of 16 to 29 nucleotides, as described hereinabove.

In some cases, the RNA sequence comprises a loop structure. In some cases, the RNA sequence comprises a stem-loop structure. In some cases, the RNA sequence comprises intramolecular base pairing. In some embodiments, the loop comprises SEQ ID NO:4. In some cases, the loop consists of SEQ ID NO:4.

In any embodiments described herein, the RNA sequence may be an aptamer. In any embodiment described herein, the nucleic acid is capable of binding to a transferrin receptor (TfR). In any embodiments described herein, the RNA sequence is capable of binding to a transferrin receptor (TfR). Thus, an RNA sequence provided herein may have at least 80% (at least 85% etc, as described hereinabove) sequence identity to SEQ ID NO:1 or SEQ ID NO:5 and a length of 16 to 29 nucleotides (as described hereinabove), and wherein the RNA sequence is capable of binding to a transferrin receptor (TfR). In any embodiment, the nucleic acid compound binds to TfR. In any embodiment, the RNA sequence binds to TfR. In any embodiment, the TfR is on a cell surface. In any embodiment, the nucleic acid compound is capable of being internalised into a cell. In any embodiment, the cell is a TfR-expressing cell.

The term "on a cell surface" as used herein refers to the location of a molecule, e.g. transferrin receptor protein, on the surface of a cell. The molecule may be associated in some way with the cell membrane. For example, the molecule may be an integral or transmembrane protein which spans the cell membrane and comprises a cytosolic domain and an extracellular domain, the molecule may be lipid anchored i.e. covalently bound to single or multiple lipid molecules in the cell membrane, or the molecule may be attached to an integral membrane protein.

The term "capable of being internalised into a cell" as used herein refers to the ability of a nucleic molecule of the present invention to be transported from the outside of a cell into a cell. This may be performed by cellular mechanisms such as endocytosis or phagocytosis. In some cases, the nucleic acids are internalised after they bind to TfR, for example by clathrin-mediated endocytosis of a TfR-nucleic acid complex (see e.g. Qian Z M et al., *Pharmacol Rev.* 2002, 54(4):561-587).

A "TfR-expressing cell" is a cell which produces TfR and displays TfR on the cell surface, e.g. as a membrane protein.

In any embodiment provided herein, the RNA sequence comprises ribonucleotide residues. In some embodiments, the RNA sequence may comprise one or more deoxyribonucleotide residues. That is, in some cases, the RNA sequence comprises one or more residues selected from deoxyadenosine monophosphate (dAMP), deoxyguanosine monophosphate (dGMP), thymidine monophosphate/deoxythymidine monophosphate (TMP/dTMP) and deoxycytidine monophosphate (dCMP). In some cases, one or more uridine monophosphate (UMP) residues in the RNA sequence are substituted for deoxythymidine monophosphate (TMP/dTMP) residues. In some embodiments, an RNA sequence with at least 80% sequence identity to SEQ ID NO:1 comprises TMP/dTMP residues at one or more or all of positions 1, 2, 3, 5, 6, 11, 12, 13, 14, 15, 19, and/or 20 of SEQ ID NO:1. In some embodiments, an RNA sequence with at least 80% sequence identity to SEQ ID NO:5 comprises dTMP residues at one or more or all of positions 2, 3, 8, 9, 10, 11, 12, and/or 16 of SEQ ID NO:5. Where an RNA sequence described herein comprises SEQ ID NO:4, said sequence may comprise dTMP residues at one or more or all of positions 4, 5, 6, 7, and/or 8 of SEQ ID NO:4. In any RNA sequence described herein, one or more of the AMP, GMP, or CMP residues may be substituted for the equivalent deoxyribonucleotide residue (i.e. dAMP, dGMP, or dCMP). In some embodiments, all ribonucleotide residues in the RNA sequence are substituted with the equivalent deoxyribonucleotide residue.

Where some, most or all of an RNA sequence is comprised of deoxyribonucleotide residues, the sequence may be described as a DNA sequence. Thus, provided herein is a nucleic acid compound comprising a DNA sequence having at least 80% sequence identity to SEQ ID NO:1 or SEQ ID NO: 5, wherein the UMP residues in SEQ ID NO:1/SEQ ID NO:5 are replaced with TMP/dTMP residues, and wherein the DNA sequence has a length of 29 nucleotides or fewer. In some embodiments, the DNA sequence is capable of binding to TfR and/or being internalised into a cell, preferably a TfR-expressing cell. In some embodiments the DNA sequence has at least 85%, at least 87%, at least 90%, at least 91%, at least 92%, at least 93%, at least 94%, at least 95%, at least 96%, at least 97%, at least 98% or at least 99% sequence identity to SEQ ID NO:1, wherein the UMP residues in SEQ ID NO:1 are replaced with dTMP residues. In some embodiments, all ribonucleotide residues in SEQ ID NO:1/SEQ ID NO:5 are substituted with the equivalent deoxyribonucleotide residue.

All embodiments described herein are applicable to a nucleic acid compound comprising a DNA sequence having at least 80% sequence identity to SEQ ID NO:1 or SEQ ID NO:5, in which the UMP residues in SEQ ID NO:1/SEQ ID NO:5 are replaced with dTMP residues, or where all ribonucleotide residues in SEQ ID NO:1/SEQ ID NO:5 are substituted with the equivalent deoxyribonucleotide residue. In such cases, the compound may be described as a deoxyribonucleic acid compound.

In some embodiments, a nucleic acid compound provided herein may comprise one or more deoxyribonucleotide residues. That is, a nucleic acid compound may comprise an RNA/DNA sequence as described hereinabove, and additionally one or more deoxyribonucleotide residues. In such cases, the compound may be described as a deoxyribonucleic acid compound.

Any nucleic/ribonucleic/deoxyribonucleic acid compound disclosed herein may be isolated and/or substantially purified.

Sequence Identity

The terms "identical" or percent "identity," in the context of two or more nucleic acid or polypeptide sequences, refer to two or more sequences or subsequences that are the same or have a specified percentage of amino acid residues or nucleotides that are the same (i.e., about 60% identity, preferably 65%, 70%, 75%, 80%, 85%, 87%, 90%, 91%, 92%, 93%, 94%, 95%, 96%, 97%, 98%, 99%, or higher identity over a specified region, when compared and aligned for maximum correspondence over a comparison window or designated region) as measured using e.g. a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 10 to 600, usually about 50 to about 200, more usually about 100 to about 150 in which a sequence may be compared to a reference sequence of the same number of contiguous positions after the two sequences are optimally aligned.

Methods of alignment of sequences for comparison are well known in the art. Optimal alignment of sequences for comparison can be conducted in various ways known to a person of skill in the art, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, PASTA, and FASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). Publicly available computer software may be used such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

Sequences

| SEQ ID NO: | DESCRIPTION | SEQUENCE |
|---|---|---|
| 1 | TR14 S1-3 (22 mer) | UUUAUUCACAUUUUUGAAUUGA |
| 2 | TR14 (87 mer) | GGGAGACAAGAAUAAACGCUCAAUGCGUUCACGUUUAUUCACAUUUUUGAAUUGAGCAUGAGCUUCGACAGGAGGCUCACAACAGGC |
| 3 | TR14 S2 (43 mer) | GGGGCUCAAUGCGUUCACGUUUAUUCACAUUUUUGAAUUGAGC |
| 4 | 8 mer loop region | ACAUUUUU |
| 5 | 16 mer truncation | AUUCACAUUUUUGAAU |
| 6 | Human transferrin receptor protein 1 isoform 1 (GI: 189458817; NCBI Reference Sequence: NP_003225.2) (GI: 189458816; NCBI Reference Sequence: NM_003234.3 (transcript variant 1)) (GI: 189458818; NCBI Reference Sequence: NM_001128148.2 (transcript variant 2) | MMDQARSAFSNLFGGEPLSYTRFSLARQVDGDNSHVEMKLAVDEEENADNNTKANVTKPKRCSGSICYGTIAVIVEFLIGFMIGYLGYCKGVEPKTECERLAGTESPVREEPGEDFPAARRLYWDDLKRKLSEKLDSTDFTGTIKLLNENSYVPREAGSQKDENLALYVENQFREFKLSKVWRDQHFVKIQVKDSAQNSVIIVDKNGRLVYLVENPGGYVAYSKAATVTGKLVHANFGTKKDFEDLYTPVNGSIVIVRAGKITFAEKVANAESLNAIGVLIYMDQTKFPIVNAELSEFGHAHLGTGDPYTPGFPSFNHTQFPPSRSSGLPNIPVQTISRAAAEKLFGNMEGDCPSDWKTDSTCRMVTSESKNVKLTVSNVLKEIKILNIFGVIKGFVEPDHYVVVGAQRDAWGPGAAKSGVGTALLLKLAQMFSDMVLKDGFQPSRSIIFASWSAGDFGSVGATEWLEGYLSSLHLKAFTYINLDKAVLGTSNFKVSASPLLYTLIEKTMQNVKHPVTGQFLYQDSNWASKVEKLTLDNAAFPFLAYSGIPAVSFCFCEDTDYPYLGTTMDTYKELIERIPELNKVARAAAEVAGQFVIKLTHDVELNLDYERYNSQLLSFVRDLNQYRADIKEMGLSLQWLYSARGDFFRATSRLTTDEGNAEKTDREVMKKLNDRVMRVEYHFLSPYVSPKESPFRHVFWGSGSHTLPALLENLKLRKQNNGAFNETLFRNQLALATWTIQGAANALSGDVWDIDNEF |
| 7 | SIRT1 saRNA sense | AUAUGUCCUCCUGGGAAGAUU |
| 8 | SIRT1 saRNA antisense | UCUUCCCAGGAGGACAUAUUU |
| 9 | CEBPA saRNA sense | GCGGUCAUUGUCACUGGUCUU |
| 10 | CEBPA saRNA antisense | GACCAGUGACAAUGACCGCUU |
| 11 | P19 | GGGAGACAAGAAUAAACGCUCAAUGGCGAAUGCCCGCCUAAUAGGGCGUUAUGACUUGUUGAGUUCGACAGGAGGCUCACAACAGGC |

Compound Moieties and Compounds

Nucleic acid compounds, e.g. ribo/deoxyribonucleic acid compounds, provided herein may comprise a therapeutic or diagnostic molecule.

The therapeutic or diagnostic molecule may form part of the nucleic acid compound provided herein, and is thus referred to as a "compound moiety", e.g. a therapeutic moiety or an imaging moiety. Alternatively, the therapeutic or diagnostic molecule may not form part of the nucleic acid compound provided herein, including embodiments thereof, but may be independently internalised by a TfR-expressing cell upon binding of a nucleic acid compound provided herein to TfR on said cell. In this situation, the therapeutic or diagnostic molecule is referred to as a "compound."

Thus, a nucleic acid compound provided herein (including embodiments thereof) may include a compound moiety. Where the nucleic acid compound includes a compound moiety, the compound moiety may be covalently (e.g. directly or through a covalently bonded intermediary) attached to the nucleic acid compound or the RNA/DNA sequence (see, e.g., useful reactive moieties or functional groups used for conjugate chemistries set forth above). Thus, in some embodiments, the nucleic acid compound further includes a compound moiety covalently attached to the nucleic acid compound or the RNA/DNA sequence. In embodiments, the compound moiety and the nucleic acid compound or the RNA/DNA sequence form a conjugate. In some embodiments, the compound moiety is non-covalently attached to the nucleic acid compound or the RNA/DNA sequence, e.g. via ionic bond(s), van der Waal's bond(s)/interactions, hydrogen bond(s), polar bond(s), "sticky bridges" (see e.g. Zhou J et al. *Nucleic Acids Res.* 2009; 37(9): 3094-3109) or combinations or mixtures thereof. The compound moiety may be attached to the nucleic acid compound or the RNA/DNA sequence via an intermediate molecule such as a modular streptavidin connector (see e.g. Chu T C et al., *Nucleic Acids Res* 2006, 34:e73). Where the compound moiety is encapsulated as described hereinbelow, e.g. in a nanoparticle or liposome, the encapsulation moiety may itself be attached, covalently or non-covalently, to the nucleic acid compound or RNA/DNA sequence.

In some embodiments, the compound moiety is a therapeutic moiety or an imaging moiety covalently attached to the nucleic acid compound or RNA/DNA sequence.

The term "therapeutic moiety" as provided herein is used in accordance with its plain ordinary meaning and refers to a monovalent compound having a therapeutic benefit (prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, nanostructures, viral capsids, cytotoxic agents (e.g. toxins) including, but not limited to ricin, doxorubicin, daunorubicin, taxol, ethidium bromide, mitomycin, etoposide, tenipo-side, vincristine, vinblastine, colchicine, dihydroxyanthra-cenedione, actinomycin D, diphtheria toxin, Pseudomonas exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is a zinc finger nuclease. In embodiments, the therapeutic moiety is a transcription activator-like effector nuclease. In embodiments, the therapeutic moiety is Cas9. The therapeutic moiety may be encapsulated in a nanoparticle or liposome, where the nanoparticle or liposome is attached to the nucleic acid compound or the RNA/DNA sequence.

In some embodiments, the therapeutic moiety is an activating nucleic acid moiety (a monovalent compound including an activating nucleic acid) or an antisense nucleic acid moiety (a monovalent compound including an antisense nucleic acid). An activating nucleic acid refers to a nucleic acid capable of detectably increasing the expression or activity of a given gene or protein. The activating nucleic acid can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid. An antisense nucleic acid refers to a nucleic acid that is complementary to at least a portion of a specific target nucleic acid and is capable of reducing transcription of the target nucleic acid or reducing the translation of the target nucleic acid or altering transcript splicing. An antisense nucleic acid may be capable of detectably decreasing the expression or activity of a given gene or protein. The antisense nucleic acid can decrease expression or activity 10%, 20%, 30%, 40%, 50%, 60%, 70%, 80%, 90% or more in comparison to a control in the absence of the antisense nucleic acid.

In some embodiments, the therapeutic moiety is an miRNA moiety (a monovalent compound including a miRNA), an mRNA moiety (a monovalent compound including an mRNA), an siRNA moiety (a monovalent compound including an siRNA) or an saRNA moiety (a monovalent compound including an saRNA). In some embodiments, the therapeutic moiety is a miRNA moiety. The term "miRNA" is used in accordance with its plain ordinary meaning and refers to a small non-coding RNA molecule capable of post-transcriptionally regulating gene expression. In one embodiment, a miRNA is a nucleic acid that has substantial or complete identity to a target gene. In some embodiments, the miRNA inhibits gene expression by interacting with a complementary cellular mRNA thereby interfering with the expression of the complementary mRNA. Typically, the miRNA is at least about 15-50 nucleotides in length (e.g., each complementary sequence of the miRNA is 15-50 nucleotides in length, and the miRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. In some embodiments, the therapeutic moiety is a siRNA moiety as described herein. In some embodiments, the therapeutic moiety is a saRNA moiety as described herein. In embodiments, the therapeutic moiety is an anticancer agent moiety. In some embodiments, the therapeutic moiety is an mRNA moiety. In embodiments, the therapeutic moiety is a cDNA moiety.

In some cases, the nucleic acid compound or the RNA/DNA sequence provided herein is attached to a sense strand of a nucleotide compound moiety e.g., mRNA, miRNA, siRNA or saRNA. In some cases the nucleic acid compound or the RNA/DNA sequence is attached to an antisense strand of a nucleotide compound moiety. In some cases, the nucleic acid compound or the RNA/DNA sequence is attached to a guide strand of a nucleotide compound moiety. In some cases, the nucleic acid compound or the RNA/DNA sequence is attached to a passenger strand of a nucleotide compound moiety.

In some embodiments, the therapeutic moiety is a C/EBPalpha saRNA moiety. A "C/EBPalpha saRNA" as provided herein is a saRNA capable of activating and/or increasing the expression of a C/EBPalpha gene and/or C/EBPalpha protein. In some cases, for example, the saRNA sequence comprises SEQ ID NO:9 and/or SEQ ID NO:10.

In some embodiments, the therapeutic moiety is a sirtuin saRNA moiety. A "sirtuin saRNA" as provided herein is a saRNA capable of activating and/or increasing the expression of a sirtuin gene, e.g. SIRT1, SIRT2, SIRT3, SIRT4, SIRT5, SIRT6 or SIRT7. In some embodiments, the therapeutic moiety is a SIRT1 saRNA moiety. A "SIRT1 saRNA" as provided herein is a saRNA capable of activating and/or increasing the expression of a SIRT1 gene and/or a Sirt1 protein. In some cases, for example, the saRNA sequence comprises SEQ ID NO:7 and/or SEQ ID NO:8.

In some embodiments, the therapeutic moiety is a HNF saRNA moiety. A "HNF saRNA" as provided herein is a saRNA capable of activating and/or increasing the expression of a HNF gene and/or protein, for example HNF4 (including isoforms and variants thereof). An HNF saRNA may be an HNF4 saRNA. That is, an HNF saRNA may be one that modulates the expression, e.g. activates and/or increases the expression, of a HNF4 gene and/or protein. In some cases, the therapeutic moiety may be NFκB (nuclear factor kappa-light-chain-enhancer of activated B cells) mRNA, miRNA, siRNA or saRNA.

In some cases, the therapeutic moiety may be a coenzyme such as NAD+/NADH (nicotinamide adenine dinucleotide), see for example Ying W, *Front Biosci.* 2007 Jan. 1; 12:1863-88.

The compound moiety provided herein may be an imaging moiety. An "imaging moiety" as provided herein is a monovalent compound detectable by spectroscopic, photochemical, biochemical, immunochemical, chemical, or other physical means. In some embodiments, the imaging moiety is covalently attached to the nucleic acid compound or the RNA/DNA sequence. Exemplary imaging moieties are without limitation $^{32}$P, radionuclides, positron-emitting isotopes, fluorescent dyes, fluorophores, antibodies, bioluminescent molecules, chemiluminescent molecules, photoactive molecules, metals, electron-dense reagents, enzymes (e.g., as commonly used in an ELISA), magnetic contrast agents, quantum dots, nanoparticles e.g. gold nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, Alexa Fluor®, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In some embodiments, the imaging moiety is a bioluminescent molecule. In some embodiments, the imaging moiety is a photoactive molecule. In some embodiments, the imaging moiety is a metal. In some embodiments, the imaging moiety is a nanoparticle.

The term "imaging agent" as used herein describes the imaging moieties above when they are not attached to the nucleic acid compounds described herein.

In some cases, the nucleic acid compounds described herein comprise (i) an RNA/DNA sequence as described herein and (ii) an additional aptamer molecule. Where said RNA/DNA sequence is an aptamer, such molecules may be described as bispecific aptamers. Preferably, the additional aptamer molecule does not target and/or bind to TfR. In some cases, the nucleic acid compounds described herein are multivalent. In some cases, a terminus of a nucleic acid as described herein may be annealed to a terminus of an additional aptamer molecule using a complementary nucleotide linker sequence attached to each moiety (see e.g. McNamara, J. O. et al. *J. Clin. Invest.* 2008 118:376-386, which is hereby incorporated by reference in its entirety).

The compound moieties or compounds described herein may be conjugated to the nucleic acid compounds of the present invention by any suitable method as described herein or known in the art, see e.g. Zhu G et al., *Bioconjug Chem.* 2015 26(11): 2186-2197, hereby incorporated by reference in its entirety. Chemical-based linkers may employ activating reagent such as m-maleimidobenzoyl N-hydroxysuccinimide ester (MBS), 2-iminothiolane (Traut's reagent), N-succinimidyl-3-2-pyridyldithio propionate (SPDP) or may use e.g. PEGylation or avidin/biotin techniques (see e.g. Pardridge W M, *Adv Drug Delivery Rev.* 1999, 36:299-321; Qian Z M et al., supra, which are hereby incorporated by reference in their entirety).

Modifications

The nucleic acid compounds described herein may contain chemical modifications, e.g. as defined herein, to enhance their functional characteristics, such as nuclease resistance or binding affinity. The modifications may be present in a nucleic acid compound, a RNA/DNA sequence and/or in a nucleotide-based compound moiety or compound, e.g. a saRNA, siRNA, miRNA, mRNA.

In some cases, modifications may be made to the base, sugar ring, or phosphate group of one or more nucleotides.

In some cases, the nucleic acid compounds described herein comprise one or more modified nucleobases. For example, the nucleic acid compounds may comprise one or more ribo/deoxyribo nucleobases modified with a fluoro (F), amino (NH$_2$) or O-methyl (OCH$_3$) group. In some cases, the nucleobases are modified at the 2' position, the 3' position, the 5' position or the 6' position. In some cases, the nucleic acid compounds may comprise one or more 2'-aminopyrimidines, 2'-fluoropyrimidines, 2'-O-methyl nucleotides and/or 'locked' nucleotides (LNA) (see e.g. Lin, Y et al., *Nucleic Acids Res.* 1994 22, 5229-5234 (1994); Ruckman, J. et al. *J. Biol. Chem.* 1998 273, 20556-20567; Burmeister, P E et al., *Chem. Biol.* 2005 12, 25-33; Kuwahara, M. & Obika, S. *Artif. DNA PNA XNA* 2013 4, 39-48; Veedu, R. N. & Wengel, J. *Mol. Biosyst.* 2009 5, 787-792). In some cases, the nucleic acid compounds comprise one or more L-form nucleic acids (see e.g. Maasch, C et al., *Nucleic Acids Symp. Ser. (Oxf.)* 2008 52, 61-62). Other suitable nucleic acid modifications will be apparent to those skilled in the art (see, e.g. Ni S et al., *Int. J. Mol. Sci* 2017 18, 1683, hereby incorporated by reference in its entirety).

In some cases, a sense and/or antisense strand of a nucleotide compound moiety, e.g., mRNA, miRNA, siRNA or saRNA, may comprise a nucleotide overhang. For example, said overhang may be a 2-nucleotide (UU) overhang. Said overhang may be on the 3' end of one or both strands. An overhang may favour Dicer recognition of the nucleotide compound moiety.

In some cases, the nucleic acid compounds described herein comprise an inverted thymidine cap on the 3' end, or comprise 3'-biotin. In some cases, the phosphodiester linkage in the nucleic acid compounds in replaced with methylphosphonate or phosphorothioate analog, or triazole linkages (see Ni S et al., supra).

In some cases, the nucleic acid compounds described herein comprise one or more copies of the C3 spacer phosphoramite. Spacers may be incorporated internally, e.g. between an RNA/DNA sequence and a compound moiety, or at the 5' or 3' end of the nucleotide sequence to attach e.g. imaging moieties.

In some cases, the nucleic acid compounds described herein comprise modifications to increase half-life and/or resist renal clearance. For example, the compounds may be modified to include cholesterol, dialkyl lipids, proteins, liposomes, organic or inorganic nanomaterials, nanoparticles, inert antibodies or polyethylene glycol (PEG) e.g. 20 kDa PEG, 40 kDa PEG. Such modifications may be at the 5'-end of the compounds. In some cases, the modification comprises a molecule with a mass above the cut-off threshold for the renal glomerulus (~30-50 kDa). In some cases, the nucleic compounds may be formulated with pluronic gel. For examples of suitable modifications and formulations see e.g. Ni et al, supra, and Zhou and Rossi, *Nat Rev Drug Disc* 2017, 16 181-202; both hereby incorporated by reference in their entirety.

The nucleic acid compounds described herein may comprise a tag, such as an albumin tag. Other tags may include: poly(His) tag, chitin binding protein (CBP), maltose binding protein (MBP), Strep-tag and glutathione-S-transferase (GST). The compounds may comprise an RNA/DNA affinity tag, as described in, for example, Srisawat C and Engelke D R, *Methods*. 2002 26(2): 156-161 and Walker et al., *Methods Mol Biol*. 2008; 488: 23-40, hereby incorporated by reference in their entirety. Other suitable tags will be readily apparent to one skilled in the art.

The nucleic acid compounds described herein may comprise spacer or linker sequences between the nucleic acid portion and a compound moiety and/or tag. Suitable spacer or linker sequences will be readily apparent to one skilled in the art.

Functional Characteristics

The nucleic acid compounds described herein may be characterised by reference to certain functional properties.

In some embodiments, any nucleic/ribonucleic/deoxyribonucleic acid compound described herein may possess one or more of the following properties:

Binds to transferrin receptor (TfR);
Capable of binding to TfR;
Binds specifically to TfR;
Capable of binding specifically to TfR;
Binds to TfR on the surface of a cell;
Capable of binding to TfR on the surface of a cell;
Capable of being internalised by a cell;
Capable of delivering a payload, e.g. compound moiety or compound, into a cell;
Capable of traversing the blood-brain barrier;
Capable of being transported into the brain;
Capable of delivering a payload, e.g. compound moiety or compound, into the brain.

The binding of a nucleic acid compound to a transferrin receptor can be determined by, e.g., surface plasmon resonance technology, as illustrated herein and described in Drescher et al., *Methods Mol Biol*. 2009; 493: 323-343.

The ability of a nucleic acid compound to be internalised by a cell or the ability to traverse the BBB can be determined using an imaging moiety conjugated to the nucleic acid compound, such as a fluorescent dye, and detecting said imaging moiety by an appropriate means. Suitable imaging methods are described herein or are well known in the art. Other methods include detecting a therapeutic moiety in brain tissue e.g. using an antibody.

The ability of a nucleic acid compound to deliver a payload into a cell can be determined by detecting the payload itself, e.g. by detection of an imaging moiety or otherwise as will be known in the art, or by detecting an effect of the successful delivery of said payload, e.g. as described herein.

The term "internalised," "internalising," or "internalisation" as provided herein refers to a composition (e.g., a compound, a nucleic acid compound, a therapeutic agent, an imaging agent) being drawn into the cytoplasm of a cell (e.g. after being engulfed by a cell membrane).

Pharmaceutical Formulations

The present invention provides pharmaceutical compositions comprising the nucleic acid compounds described herein.

The nucleic acid compounds described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion. Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some cases, the nucleic acid compound according to the present invention are formulated for injection or infusion, e.g. into a blood vessel or tumour.

Pharmaceutical compositions of the nucleic acid compounds provided herein may include compositions having a therapeutic moiety contained in a therapeutically or prophylactically effective amount, i.e., in an amount effective to achieve its intended purpose. The pharmaceutical compositions of the nucleic acid compounds provided herein may include compositions having imaging moieties contained in an effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically or prophylactically effective amount of a therapeutic moiety provided herein is well within the capabilities of those skilled in the art, especially in light of the detailed disclosure herein. When administered in methods to diagnose or detect a disease, such compositions will contain an amount of an imaging moiety described herein effective to achieve the desired result, e.g., detecting the absence or presence of a target molecule, cell, or tumour in a subject. Determination of a detectable amount of an imaging moiety provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease; the route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the nucleic acid compounds provided, as well as combinations of an anticancer agent and the nucleic acid compound provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In one aspect, provided herein is a pharmaceutical composition including a nucleic acid compound as described herein, including embodiments thereof, and a pharmaceutically acceptable excipient. In some embodiments, the nucleic acid includes a compound moiety covalently attached to the nucleic acid compound or the RNA/DNA sequence. As described above, the compound moiety may be a therapeutic moiety or an imaging moiety covalently attached to the nucleic acid compound or the RNA/DNA sequence.

In some aspects, the pharmaceutical composition includes a nucleic acid compound as provided herein, including embodiments thereof, and a therapeutic agent. In some embodiments, the nucleic acid compound comprises a compound moiety. In some embodiments, the nucleic acid compound and the therapeutic agent are not covalently attached. A therapeutic agent as provided herein refers to a composition (e.g. compound, drug, antagonist, inhibitor, modulator) having a therapeutic effect. In some embodiments, the therapeutic agent is an anticancer agent. In some embodiments, the pharmaceutical composition includes a pharmaceutically acceptable excipient.

In some aspects, there is provided a pharmaceutical composition comprising a nucleic acid compound as provided herein, including embodiments thereof, and a compound as described herein. That is, the composition comprises the nucleic acid compound and a compound, e.g. a therapeutic or diagnostic molecule, which does not form part of the nucleic acid compound itself. In some cases, the nucleic acid compound comprises a compound moiety. In some cases, the pharmaceutical composition additionally comprises a therapeutic agent.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavours, salt solutions (such as Ringer's solution), alcohols, oils, gelatins, carbohydrates such as lactose, amylose or starch, fatty acid esters, hydroxymethylcellulose, polyvinyl pyrrolidine, and colours, and the like. Such preparations can be sterilized and, if desired, mixed with auxiliary agents such as lubricants, preservatives, stabilizers, wetting agents, emulsifiers, salts for influencing osmotic pressure, buffers, colouring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "composition" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical composition is optionally in unit dosage form. In such form the preparation is subdivided into unit doses containing appropriate quantities of the active component. The unit dosage form can be a packaged composition, the package containing discrete quantities of composition, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Delivery

As described above the nucleic acid compounds, e.g. ribo/deoxyribonucleic acid compounds provided herein, including embodiments thereof, may be used to deliver compound moieties or compounds (e.g., therapeutic agents or imaging agents) into a cell. Where a compound moiety (e.g., therapeutic moiety or imaging moiety) is delivered into a cell, the compound moiety may be covalently attached to the nucleic acid compound provided herein including embodiments thereof. Upon binding of the nucleic acid compound to TfR on a cell, the compound moiety may be internalized by the cell while being covalently attached to the nucleic acid compound. Thus, in one aspect, a method of delivering a compound moiety into a cell is provided. The method includes, (i) contacting a cell with the nucleic acid compound, or composition, as provided herein including embodiments thereof and (ii) allowing the nucleic acid compound to bind to a TfR on the cell and pass into the cell thereby delivering the compound moiety into the cell.

Alternatively, where a compound is delivered into a cell, the compound (e.g., a therapeutic agent or an imaging agent) may not be covalently attached to the nucleic acid compound. Upon binding of the nucleic acid compound provided herein, including embodiments thereof, to TfR on a cell, the nucleic acid compound and the compound provided may be internalized by the cell without being covalently attached to each other. Thus, in another aspect, a method of delivering a compound into a cell is provided. The method includes (i) contacting a cell with a compound and the nucleic acid compound, or composition, as provided herein including embodiments thereof and (ii) allowing the nucleic acid compound to bind to a TfR on the cell and the compound to pass into the cell thereby delivering the compound into the cell. In embodiments, the compound is a therapeutic agent or imaging agent. In embodiments, the compound is non-covalently attached to the nucleic acid compound.

The methods may be performed in vitro, ex vivo, or in vivo. In some cases, the methods comprise delivering the compound moiety or compound across the blood-brain barrier into the brain.

Therapeutic and Prophylactic Applications

The nucleic acid compounds, e.g. ribo/deoxyribonucleic acid compounds, and compositions provided herein find use in therapeutic and prophylactic methods.

The present invention provides nucleic acid compounds and compositions described herein for use in a method of medical treatment or prophylaxis. The invention also provides the use of nucleic acid compounds and compositions described herein in the manufacture of medicaments for treating or preventing a disease or disorder. The invention described herein also provides methods of treating or preventing a disease or disorder, comprising administering to a subject in need thereof a therapeutically or prophylactically effective amount of a nucleic acid compound or composition described herein.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The nucleic acid compounds described herein find use in the treatment or prevention of any disease/disorder which would benefit from the delivery of said compounds, and/or associated therapeutic or imaging moieties, to cells expressing TfR. The nucleic acid compounds also find use in the treatment or prevention of any disease/disorder which would benefit from the delivery of said compounds and/or associated moieties to the brain.

It will be appreciated that the therapeutic and prophylactic utility of the present invention extends to the treatment of any subject that would benefit from the delivery of a compound moiety or compound into a cell expressing TfR, or into the brain.

In some embodiments, the disease/disorder is one which would benefit from the activation of a Sirtuin gene/protein e.g. SIRT1, the activation of a C/EBPalpha gene/protein, and/or the activation of a HNF gene/protein. In some embodiments, the nucleic acids and compositions described herein find use to treat or prevent cancer, metabolic disorders, or neurological disorders.

For example, in some embodiments, certain methods described herein treat cancer (e.g. liver cancer (e.g. hepatocellular carcinoma), pancreatic cancer, pancreatic liver metastases, prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. liver cancer (e.g. hepatocellular carcinoma), pancreatic cancer, pancreatic liver metastases, prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

In some embodiments, the cancer is a cancer as described herein. In some embodiments, the cancer is liver cancer e.g. hepatocellular carcinoma, pancreatic cancer, pancreatic liver metastases, metastatic cancer, or brain cancer.

In some cases, the cancer is one in which activation of a Sirtuin gene/protein e.g. SIRT1, activation of a C/EBPalpha gene/protein, and/or activation of a HNF gene/protein has a therapeutic or prophylactic effect.

In some embodiments, the methods of treatment described herein comprise administering to a subject in need thereof a therapeutically or prophylactically effective amount of a nucleic acid compound or composition as described herein, wherein the nucleic acid compound comprises an anticancer therapeutic moiety. In some embodiments, the methods of treatment further comprise administering to a subject in need thereof an effective amount of an anticancer agent.

In some cases, the methods of treatment described herein comprise inducing or inhibiting autophagy, for example through the activation or inhibition of Beclin1. See e.g. Jin and White, *Autophagy* 2007; 3(1):28-31; Rosenfeldt and Ryan, *Expert Rev Mol Med.* 2009; 11:e36; and Mah and Ryan, *Cold Spring Harb Perspect Biol.* 2012; 4(1): a008821, all hereby incorporated by reference in their entirety. In some cases, the methods of treatment described herein comprise inducing or inhibiting the activity of nuclear factor kappa-light-chain-enhancer of activated B cells (NF-κB).

In some embodiments, the disease/disorder is a metabolic disorder. For example, the metabolic disorder may be metabolic syndrome, type I diabetes mellitus, type 2 diabetes mellitus, dyslipidemia, impaired fasting glucose, impaired glucose tolerance, obesity, cardiovascular disease, insulin resistance, hypertriglyceridemia, psoriasis, psoriatic arthritis, coronary vascular diseases e.g. coronary heart disease, coronary artery disease, stroke and peripheral artery disease, atherosclerosis, fatty liver disease, non-alcoholic fatty liver disease (NAFLD), steatohepatitis, and/or lipodystrophic disorders.

In some cases, the metabolic disorder is one in which activation of a Sirtuin gene/protein, activation of a C/EBPalpha gene/protein, and/or activation of a HNF gene/protein has a therapeutic or prophylactic effect.

In some cases, the nucleic acids and compositions of the present invention find use in the reduction of body weight, reduction of body weight gain, reduction of serum glucose, regulating glucose homeostasis, decreasing insulin resistance, reduction of white adipose tissue, reduction of cholesterol, reduction of low-density lipoprotein (LDL), increasing high-density lipoprotein (HDL), increasing high-density lipoprotein/low-density lipoprotein (HDL/LDL) ratio, reduction of serum triglycerides.

In some cases, the nucleic acids and compositions of the present invention find use in targeting TfR-expressing cells in the pancreas, brain, heart, white and brown adipose tissue, muscle, and/or liver.

In some embodiments, the disease/disorder is a neurological disorder. For example, the neurological disorder may be Alzheimer's disease, amyotrophic lateral sclerosis (ALS), motor neuron disease, Parkinson's disease, Huntington's disease, spinal and bulbar muscular atrophy (SBMA).

In some cases, the neurological disorder is one in which activation of a Sirtuin gene/protein, activation of a C/EBPalpha gene/protein, and/or activation of a HNF gene/protein has a therapeutic or prophylactic effect.

In some cases, the nucleic acids and compositions of the present invention find use in the treatment or prevention of, i.e. reduction of or protection against, neurodegeneration.

Where combination treatments are contemplated, it is not intended that the agents (i.e. nucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount". A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Patient", "subject" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In some embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Methods of Detecting a Cell

The nucleic acid compositions, e.g. ribo/deoxyribonucleic acid compounds, provided herein may also be used for the delivery of compounds and compound moieties to a cell expressing TfR. As described above, the compounds and compound moieties delivered may be imaging agents useful for cell detections. Thus, in one aspect, a method of detecting a cell is provided. The method includes (i) contacting a cell with the nucleic acid compound, or composition, as provided herein including embodiments thereof, wherein the nucleic acid compound further includes an imaging moiety, (ii) the nucleic acid compound, or composition, is allowed to bind to a transferrin receptor on the cell and pass into the cell, (iii) the imaging moiety is detected thereby detecting the cell.

In another aspect, a method of detecting a cell is provided. The method includes (i) contacting a cell with an imaging agent and the nucleic acid compound, or composition, as provided herein including embodiments thereof, (ii) the nucleic acid compound, or composition, is allowed to bind to a transferrin receptor on the cell and the imaging agent is allowed to pass into the cell, (iii) the imaging agent is detected thereby detecting the cell.

In some cases, the cell is a malignant cell. In some cases, the cell is a breast cancer cell. In some cases, the cell is a prostate cancer cell. In some cases, the cell is a liver cancer cell. In some cases, the cell is a pancreatic cancer cell. In some cases, the cell is a brain cancer cell. In some cases, the cell is a non-malignant cell. In some cases, the cell is a brain cell. In some cases, the cell forms part of an organism. In some cases, the organism is a mammal. In some cases, the cell forms part of a cell culture.

The methods may be performed in vitro, ex vivo, or in vivo. In some cases, the methods comprise delivering the compound moiety or compound across the blood-brain barrier into the brain.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Aspects and embodiments of the present invention will now be discussed with reference to the accompanying figures. Further aspects and embodiments will be apparent to those skilled in the art.

BRIEF DESCRIPTION OF THE DRAWINGS

Embodiments and experiments illustrating the principles of the invention will now be discussed with reference to the accompanying figures.

(FIG. 4A) Neuronal tissue from control rats shows blue negative staining. (FIG. 4B) Neuronal tissue from rats injected with TfR-SIRT1 saRNA shows brown nuclear staining to SIRT1.

(FIG. 7A) Mice treated with TfR-CEBPA or P19-CEBPA show reduced tumour growth (determined by reduced photon increase). (FIG. 7B) Mice treated with TfR-CEBPA or P19-CEBPA show reduced tumour volume.

(FIG. 8A) Rats treated with TfR-SIRT did not gain weight. (FIG. 8B) Rats treated with TfR-SIRT had reduced white adipose tissue. (FIG. 8C) Rats treated with TfR-SIRT showed reduced total cholesterol. (FIG. 8D) Rats treated with TfR-SIRT showed reduced low density lipoprotein (LDL) cholesterol level. (FIG. 8E) Rats treated with TfR-SIRT showed an increased high density lipoprotein (HDL)/LDL ratio. (FIG. 8F) Rats treated with TfR-SIRT showed reduced fasting blood glucose levels.

EMBODIMENTS

Figure 1:
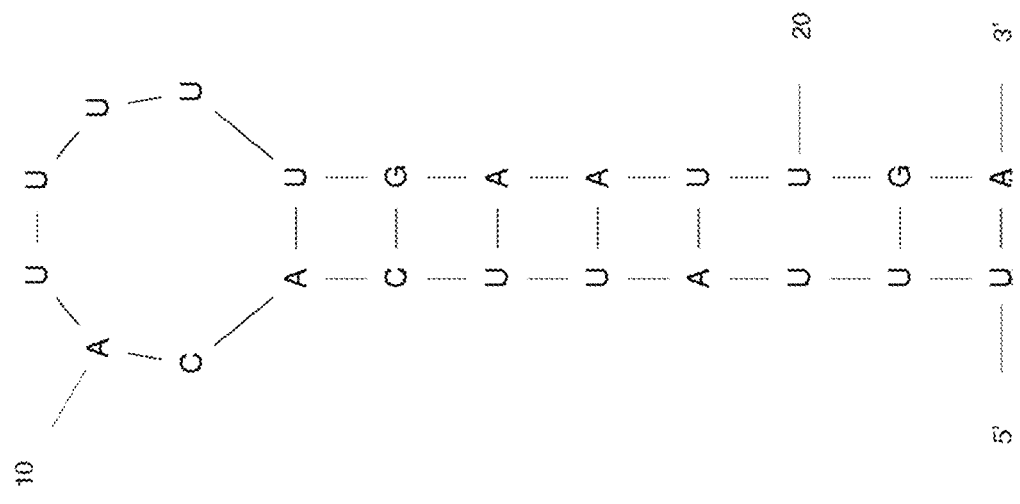
FIG. 1. Predicted Mfold structures of aptamer TR14 S1-3 (TfR; SEQ ID NO:1).
Figure 1:
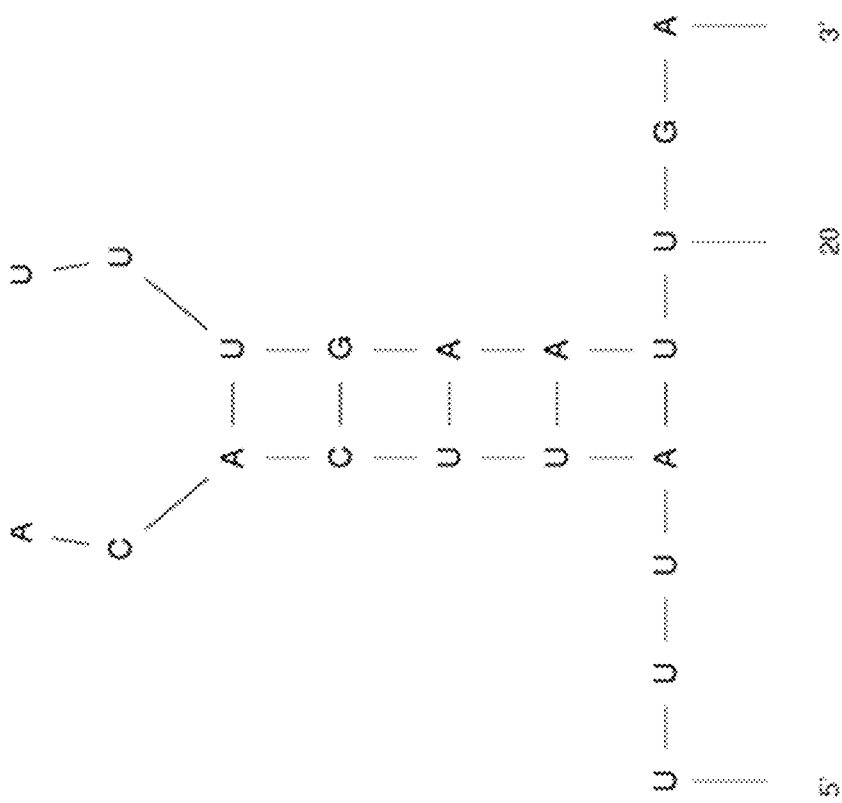

Embodiments include but are not limited to embodiments P1 to P32 following:

Embodiment P1. A ribonucleic acid compound comprising, or consisting of, an RNA sequence having at least 90% sequence identity to SEQ ID NO:1, wherein said RNA sequence has a length of 29 nucleotides or fewer, and wherein the RNA sequence is capable of binding to a transferrin receptor (TfR).

Embodiment P2. The ribonucleic acid compound according to embodiment P1, wherein said RNA sequence has a length of 22 nucleotides or fewer.

Embodiment P3. The ribonucleic acid compound according to embodiment P1 or embodiment P2, wherein said RNA sequence is 22 nucleotides in length.

Embodiment P4. The ribonucleic acid compound according to any one of embodiments P1 to P3, wherein the RNA sequence has 100% sequence identity to SEQ ID NO:1.

Embodiment P5. A ribonucleic acid compound comprising, or consisting of, an RNA sequence having at least 90% sequence identity to SEQ ID NO:5, wherein said RNA sequence has a length of 29 nucleotides or fewer, and wherein the RNA sequence is capable of binding to a transferrin receptor (TfR).

Embodiment P6. The ribonucleic acid compound according to embodiment P5, wherein said RNA sequence is 16 nucleotides in length.

Embodiment P7. The ribonucleic acid compound according to embodiment P5 or embodiment P6, wherein the RNA sequence has 100% sequence identity to SEQ ID NO:5.

Embodiment P8. The ribonucleic acid compound according to any one of embodiments P1 to P7, wherein the RNA sequence is capable of binding to TfR on a cell surface.

Embodiment P9. The ribonucleic acid compound according to any one of embodiments P1 to P8, which is capable of being internalised into a cell.

Embodiment P10. The ribonucleic acid compound according to any one of embodiments P1 to P9, which is capable of traversing the blood-brain barrier.

Embodiment P11. The ribonucleic acid compound according to any one of embodiments P1 to P10, further comprising a compound moiety attached to said RNA sequence.

Embodiment P12. The ribonucleic acid compound according to embodiment P11, wherein the compound moiety is a therapeutic moiety or an imaging moiety.

Embodiment P13. The ribonucleic acid compound according to embodiment P11 or embodiment P12, wherein said compound moiety is covalently attached to said RNA sequence.

Embodiment P14. The ribonucleic acid compound according to embodiment P12 or embodiment P13, wherein said therapeutic moiety is a nucleic acid moiety, a peptide moiety or a small molecule drug moiety.

Embodiment P15. The ribonucleic acid compound according to embodiment P14, wherein said therapeutic moiety is an activating nucleic acid moiety or an antisense nucleic acid moiety.

Embodiment P16. The ribonucleic acid compound according to embodiment P14 or embodiment P15, wherein said therapeutic moiety is a miRNA, mRNA, saRNA or siRNA moiety.

Embodiment P17. The ribonucleic acid compound according to any one of embodiments P12 to P16, wherein said therapeutic moiety is an anticancer therapeutic moiety.

Embodiment P18. The ribonucleic acid compound according to any one of embodiments P12 to P17, wherein said therapeutic moiety is a C/EBPalpha saRNA moiety, a SIRT1 saRNA moiety, or a HNF saRNA moiety.

Embodiment P19. The ribonucleic acid compound according to any one of embodiments P11 to P13, wherein the imaging moiety is a bioluminescent molecule, a photoactive molecule, a metal or a nanoparticle.

Embodiment P20. A pharmaceutical composition comprising a ribonucleic acid compound according to any one of embodiments P1 to P19, optionally comprising a pharmaceutically acceptable excipient.

Embodiment P21. The pharmaceutical composition according to embodiment P20, further comprising a therapeutic agent, optionally an anticancer agent.

Embodiment P22. A method of delivering a compound moiety into a cell, the method comprising:
(i) contacting a cell with the ribonucleic acid compound according to any one of embodiments P11 to P19 or a composition according to embodiment P20 or embodiment P21; and
(ii) allowing said ribonucleic acid compound to bind to a transferrin receptor on said cell and pass into said cell thereby delivering said compound moiety into said cell.

Embodiment P23. A method of delivering a compound into a cell, the method comprising:
(i) contacting a cell with a compound and the ribonucleic acid compound according to any one of embodiments P1 to P10; and
(ii) allowing said ribonucleic acid compound to bind to a transferrin receptor on said cell and pass into said cell thereby delivering said compound into said cell.

Embodiment P24. The method according to embodiment P23, wherein said compound is a therapeutic agent or an imaging agent.

Embodiment P25. A ribonucleic acid compound according to any one of embodiments P1 to P19, or the composition according to embodiment P20 or embodiment P21, for use in a method of medical treatment or prophylaxis.

Embodiment P26. Use of a ribonucleic acid compound according to any one of embodiments P1 to P19, or the composition according to embodiment P20 or embodiment P21, in the manufacture of a medicament for treating or preventing a disease or disorder.

Embodiment P27. A method of treating or preventing a disease or disorder, the method comprising administering to a subject in need thereof an effective amount of a ribonucleic acid compound according to any one of embodiments P1 to P19, or a composition according to embodiment P20 or embodiment P21.

Embodiment P28. The ribonucleic acid compound or composition for use according to embodiment P25, the use of the ribonucleic acid compound or composition according to embodiment P26, or the method according to embodiment P27, wherein the disease or disorder is cancer.

Embodiment P29. The ribonucleic acid compound or composition for use, the use of the ribonucleic acid compound or composition, or the method according to embodiment P28, wherein the method further comprises administering an anticancer agent.

Embodiment P30. The ribonucleic acid compound or composition for use according to embodiment P25, the use of the ribonucleic acid compound or composition according to embodiment P26, or the method according to embodiment P27, wherein the disease or disorder is a metabolic disorder or a neurological disorder.

Embodiment P31. A method of detecting a cell, the method comprising:
(i) contacting a cell with the ribonucleic acid compound according to any one of embodiments P1 to P13, or embodiment P19, or the composition according to embodiment P20, wherein the ribonucleic acid compound comprises an imaging moiety;
(ii) allowing said ribonucleic acid compound to bind to a transferrin receptor on said cell and pass into said cell; and
(iii) detecting said imaging moiety thereby detecting said cell.

Embodiment P32. A method of detecting a cell, the method comprising:

(i) contacting a cell with an imaging agent and the ribonucleic acid compound according to any one of embodiments P1 to P10;

(ii) allowing said ribonucleic acid compound to bind to a transferrin receptor on said cell and said imaging agent to pass into said cell; and (iii) detecting said imaging agent thereby detecting said cell.

EXAMPLES

Example 1

Selection and Characterisation of TfR Aptamers

Aptamers capable of binding to the extracellular domain of TfR were identified by protein SELEX (systemic evolution of ligands by exponential enrichment), basically as described by Tuerk and Gold (Tuerk, C., Methods Mol Biol., 67, 219-230 (1997), and as described in the Examples of WO 2006/061386.

A library of 2'F RNAs was used to increase nuclease-resistance and enhance aptamer folding. To isolate 2'F RNA aptamers binding to intact cells, a library of approximately $4^{40}$ different 2'F RNA molecules, containing a 40-nt-long random sequence flanked by defined sequences, was screened by SELEX. After 12 cycles of selection, the highly enriched aptamer pools were cloned.

An 87-nucleotide TfR RNA aptamer (TR14; SEQ ID NO:2) and a 43-nucleotide TfR RNA aptamer (TR14 S2; SEQ ID NO:3) were identified and characterised, as described in WO 2006/061386. The binding affinity of both TR14 and TR14 S2 aptamers for TfR was measured using surface plasmon resonance (SPR) technology. The results are replicated in Table 1. TR14 and TR14 S2 were found to be capable of being internalised into human liver cancer cells (HepG2; ATCC® HB-8065™).

TABLE 1

| Kinetics of TR14 and TR14 S2. | | | |
|---|---|---|---|
| Name | ka (1/Ms) | kd (1/s) | $K^D$ (M) |
| TR14 (87-nt) | 3.70E+07 | 1.17E−03 | 3.17E−11 |
| TR14 S2 (43-nt) | 8.34E+08 | 5.77E−04 | 6.92E−13 |

Example 2

A 22-Nucleotide TfR Aptamer

A smaller truncated version of the TR14 aptamer was synthesised (SEQ ID NO:1). This 22-nucleotide TfR aptamer was designated "TR14 S1-3". The structure of TR14 S1-3 was predicted using Mfold software (Zuker M, Nucleic Acids Res. 2003 Jul. 1; 31(13):3406-15), and available at http://unafold.rna.albany.edu/?q=mfold. The Mfold predicted structures for TR14 S1-3 are shown in FIG. 1.

The kinetics of TR14 S1-3 were analysed by surface plasmon resonance (SPR) technology. The Biacore T100 (GE Healthcare, Uppsala, Sweden) was used to monitor label-free the aptamer-transferrin receptor interactions in real time. Biotinylated aptamers were coupled to a streptavidin-coated Biocore chip (SensorChip SA, BR-1003-98, General Electric Company) by an injection in binding buffer at concentration of 25 μg/mL (30 mM Tris-HCl, pH 7.5, 150 mM NaCl, 5 mM MgCl2) at 10 uL/min. The RNA was refolded by heating to 65° C. followed by cooling to 37° C. before immobilization. To measure binding kinetics, five concentrations of purified transferrin receptor protein were injected at a flow rate of 10 uL per minute. After binding, the surface was regenerated by injecting 50 mM NaOH at flow rate of 15 μL per minutes for 20 seconds. Data from the control surface were subtracted. BIAevaluation software (GE Healthcare) was used for analysis. The binding data were fit to a 1:1 binding with a mass transfer model to calculate kinetic parameters.

Figure 2:
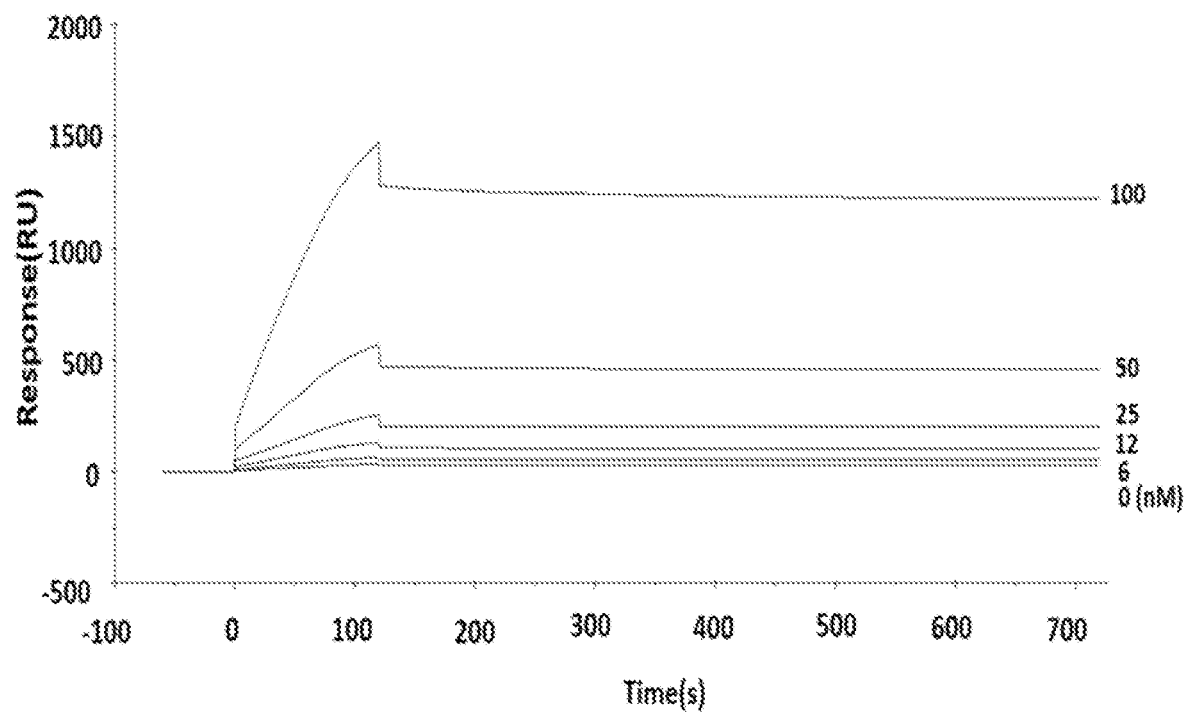
FIG. 2. Kinetics of aptamer TR14 S1-3 binding to transferrin receptor.

The results are shown in FIG. 2. The 22-nucleotide TR14 S1-3 aptamer binds to transferrin receptor protein with Ka, Kd and $K_D$ values in a similar range to TR14.

Example 3

Binding of TR14 S1-3 to TfR and Internalisation into Cells

The 22-nucleotide aptamer TR14 S1-3 was assessed for its ability to bind transferrin receptor and be internalised into cells.

Three cancer cell lines were tested:
Human liver cancer cells (HepG2, ATCC® HB-8065™)
Human pancreatic cancer cells (PANC-1, ATCC® CRL-1469)
Mouse pancreatic cancer cells (LTPA, ATCC® CRL-2389).

$1 \times 10^5$ cells were seeded in 35 mm glass-bottom dishes (MatTek, Ashland, Mass.) and grown in appropriate media for 24 hours. Aptamer RNAs were labeled with Cy3 fluorescent dye using the Cy3 Silencer siRNA labeling kit (Thermo Fisher Scientific, Waltham, Mass.). Cy3-labeled aptamers in binding buffer (30 mM Tris-HCl, pH 7.5, 150 mM NaCl, 5 mM $MgCl_2$) were added to the cells at 200 nM and incubated for 2 hours. Before imaging, cells were washed with DPBS twice. Live-cell confocal imaging was performed with a Zeiss LSM 510 Meta inverted two-photon confocal microscope system using a C-Apo 40×/1.2NA water immersion objective, and AIM 4.2 software (Carl Zeiss, Jena, Germany).

Figure 3:
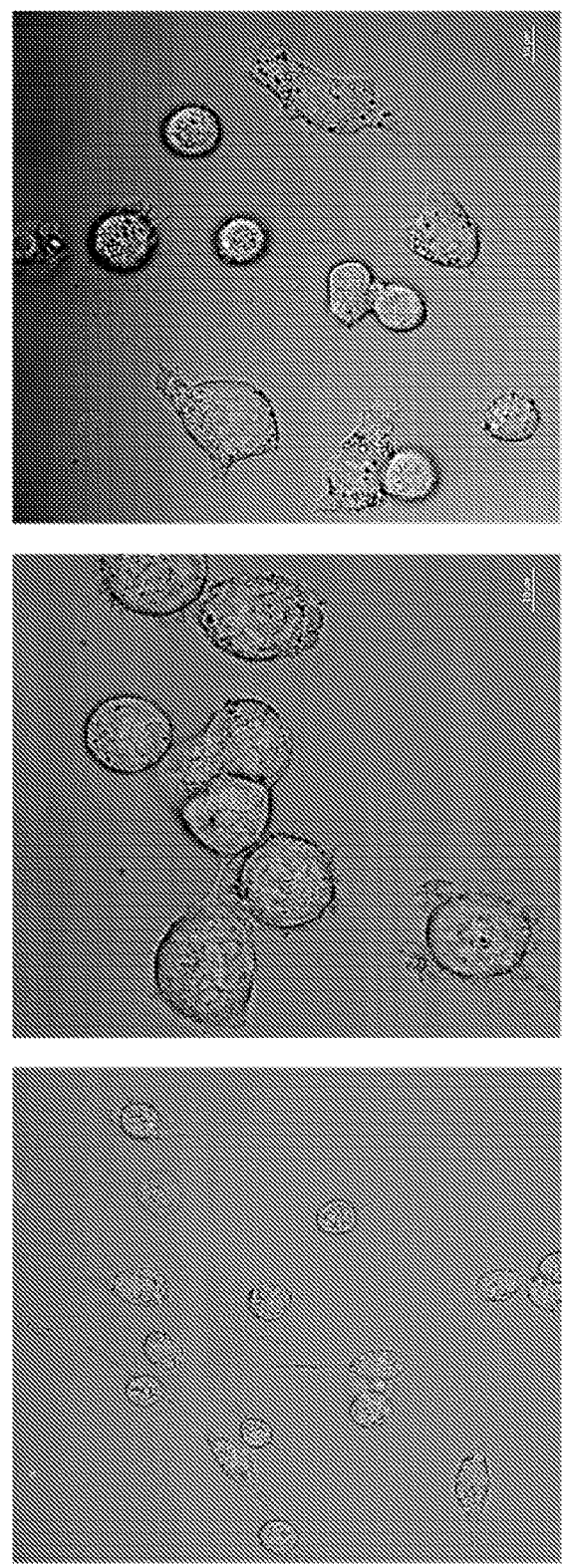
FIG. 3. Internalisation of aptamer TR14 S1-3 into human liver cancer cells (HepG2), human pancreatic cancer cells (PANC-1) and mouse pancreatic cancer cells (LTPA).

The results are shown in FIG. 3. All three cancer cell lines (human HepG2, human PANC-1, and murine LTPA) internalised the TfR-bound TR14 S1-3 aptamer, showing that TR14 S1-3 is cross-reactive between species.

TR14 S1-3 Aptamer can Cross the Blood-Brain Barrier

The 22-nucleotide aptamer TR14 S1-3 was assessed for its ability to cross the blood-brain barrier in vivo.

A ribonucleic acid was synthesised comprising TR14 S1-3 (TfR; SEQ ID NO:1), five C3 (phosphoramidite) spacers and a SIRT1 saRNA. The sense and antisense strands of the SIRT1 saRNA are shown in SEQ ID NO:7 and SEQ ID NO:8, respectively. The sense and antisense sequences each comprise a 2-nucleotide (UU) overhang at the 3' end.

Rats were treated with TfR-SIRT1 saRNA or a control via tail injection. Neuronal tissue from both groups was isolated and contacted with a SIRT1 monoclonal antibody to detect whether circulating TfR could deliver the SIRT1 saRNA cargo to the brain.

Figure 4A:
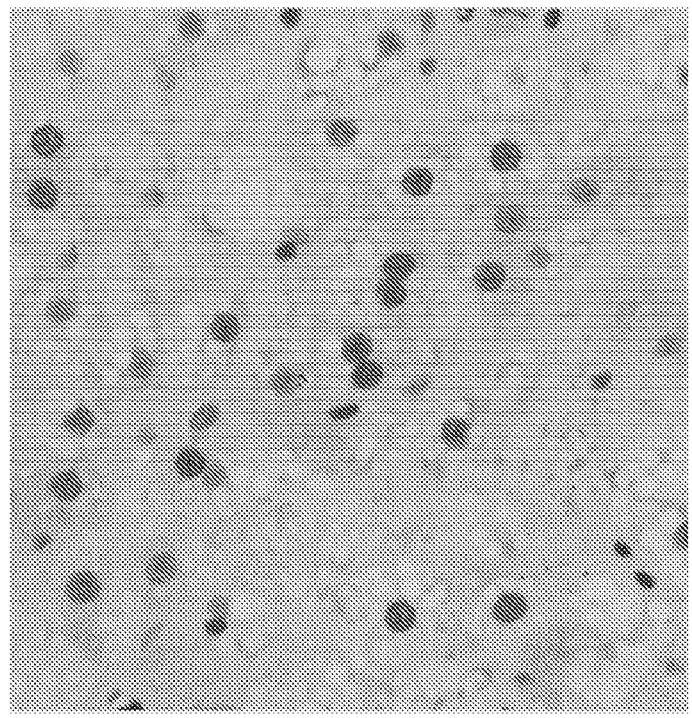
FIGS. 4A and 4B. Immunohistochemical staining of neuronal tissue from rat brains showing the ability of TR14 S1-3 (TfR) to cross the blood-brain barrier. SIRT1 expression was detected using a SIRT1 monoclonal antibody.
Figure 4B:
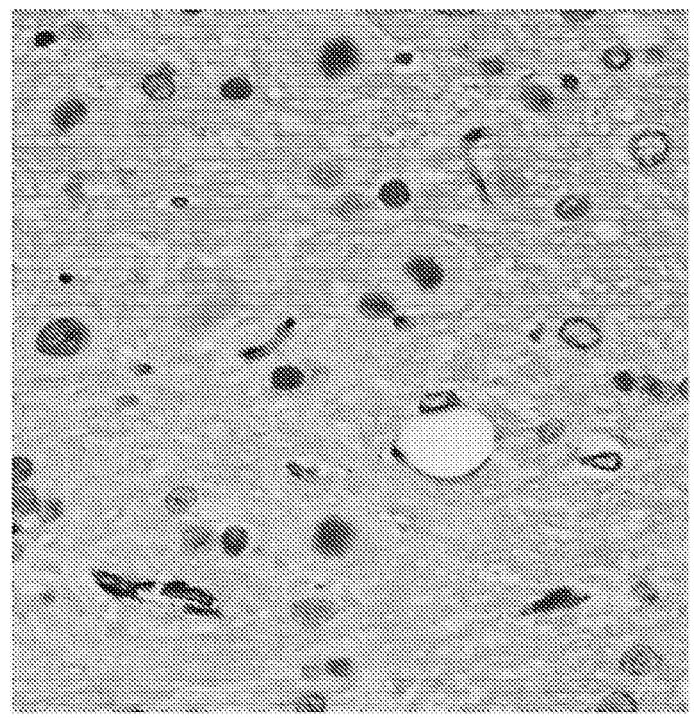

The results are shown in FIGS. 4A and 4B. Neuronal tissue from control rats (4A) shows blue negative staining, whereas neuronal tissue from rats injected with the TfR-SIRT1 saRNA ribonucleic acid compound (4B) shows brown nuclear staining to SIRT1.

This suggests that the aptamer has crossed the blood-brain barrier and entered nuclei in the neuronal tissue. This demonstrates that TR14 S1-3 could provide a mechanism for delivering therapeutic and imaging payloads into the brain.

Example 4

TR14 S1-3 Aptamer Delivers Payloads In Vivo to Cancer Cells

The ability of TR14 S1-3 aptamer to deliver therapeutic payloads in vivo was assessed.

A ribonucleic acid was synthesised comprising TR14 S1-3 (TfR; SEQ ID NO:1), five C3 (phosphoramidite) spacers and a CEBPA or HNF saRNA. The sense and antisense sequences of the CEBPA saRNA are shown in SEQ ID NO:9 and SEQ ID NO:10, respectively. The sense and antisense sequences each comprise a 2-nucleotide (UU) overhang at the 3' end.

Diethylnitrosamine (DEN)-Induced Hepatocellular Carcinoma (HCC) Model in Rats

Male Wistar rats (~200 g) at 7 weeks of age were obtained from BioLASCO Taiwan Co., Ltd. The rats were housed in standard conditions, and all the experiments were conducted in accordance with the "Guide for the Care and Use of Laboratory Animals" prepared by the Institutional Animal Care and Use Committee of National Taiwan University. All rats were given 100 ppm (vol/vol) DEN solution daily (Sigma, St Louis, Mo.) as the sole source of drinking water for 9 weeks, followed by 3 weeks of regular water. The average body weight of the animals was measured once a week per group of five rats, and the concentration of DEN in their drinking water was adjusted in proportion to the body weight each week relative to that of the first week. For example, if the average body weight values at weeks 1, and 5 of DEN administration were 200, and 300 g (1.5-fold), respectively, then the DEN concentration in the drinking water was set at 100 and 150 ppm, respectively.

For in vivo therapy, animals were used that had been exposed to DEN solution for 9 weeks. The rats were randomly divided into 4 groups: PBS group, TfR group, TfR-CEBPA group, and TfR-HNF group (n>5 in each group). PBS, TfR, TfR-CEBPA and TfR-HNF were injected via tail vein 3 times/week for 3 weeks. The rats were sacrificed two days after last injection by $CO_2$, and the livers were removed then stored for following analysis. Blood samples were collected from heart and were centrifuged at room temperature for 15 min at 3000 rpm and the serum were preserved at −80° C. until assayed.

After sacrifice, all liver lobes were promptly removed and weighed, and the diameters of all of the macroscopically visible nodules on the liver surface and in the 5-mm sliced sections were measured. Tumour burden was determined in terms of the total volume of all the tumour nodules with diameter >3 mm.

The complete blood count (CBC) test was performed by hematology analyzer Sysmex HST-N402XE (Sysmex, Japan). The serum levels of bilirubin (higher levels indicate liver dysfunction) were measured with VITROS 5,1 FS Chemistry System (Ortho Clinical Diagnostics, USA).

Figure 5A:
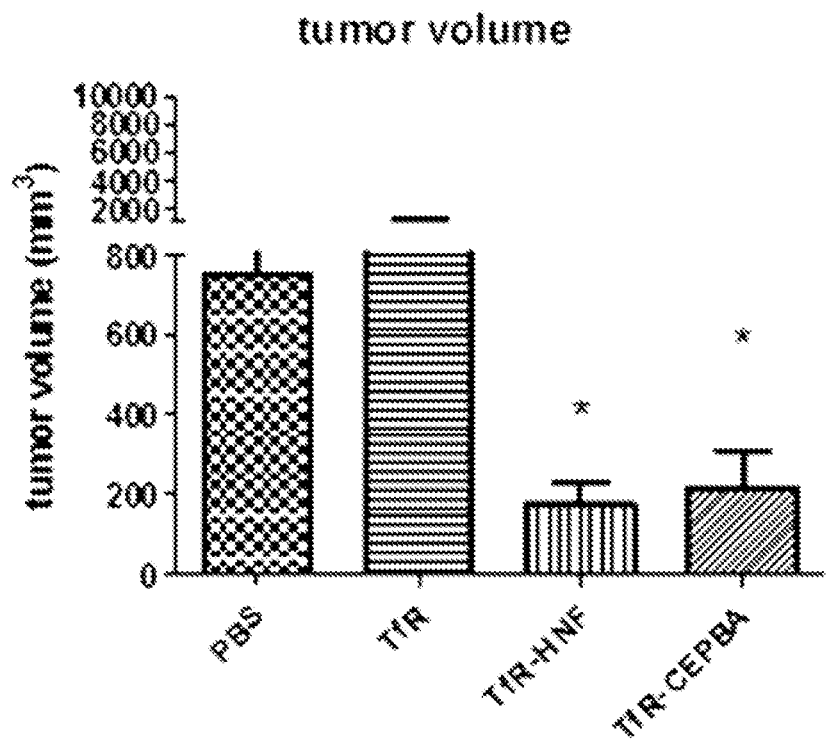
FIGS. 5A and 5B. Graphs showing the effect of TfR-CEBPA and TfR-HNF treatment compared to PBS and TfR-alone controls in a diethylnitrosamine (DEN)-induced hepatocellular carcinoma (HCC) model in male Wistar rats. TfR-CEBPA and TfR-HNF saRNA treatment reduced tumour volume (FIG. 5A) and reduce levels of bilirubin in the blood (FIG. 5B).
Figure 5B:
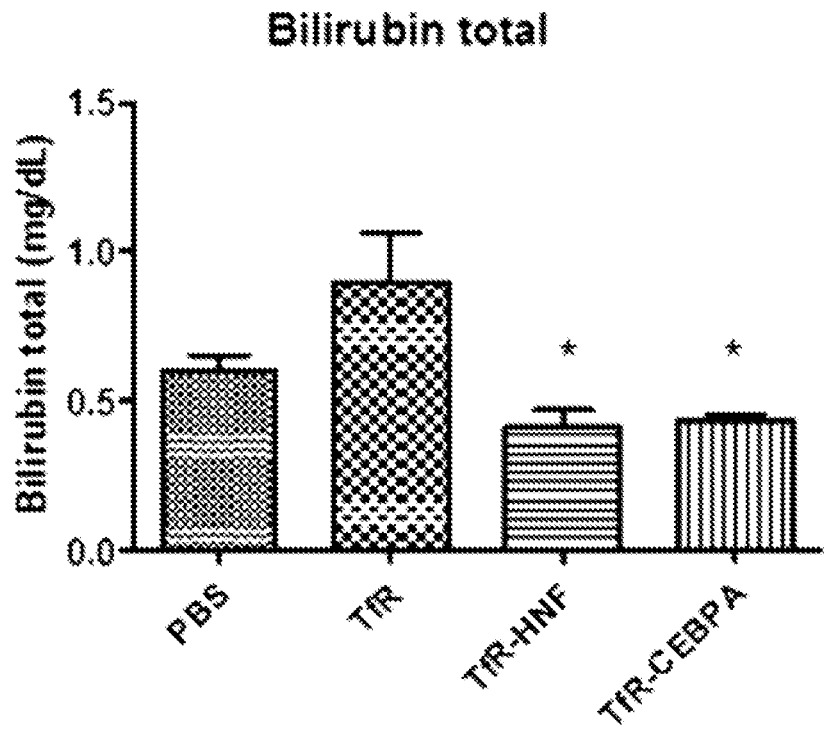

The results are shown in FIGS. 5A and 5B. Rats that received treatment with TfR-CEBPA or TfR-HNF showed significantly reduced tumour burden (tumour volume) compared with rats that received PBS or TfR alone (FIG. 5A). Rats treated with TfR-CEBPA or TfR-HNF also showed significantly lower levels of bilirubin in the blood, illustrating improved liver function compared to the control treatments (FIG. 5B).

Hepatic Epithelial Cell Tumour Model in Rats

Male F344 rats (~200 g) at 7 weeks of age were obtained from BioLASCO Taiwan Co., Ltd. The rats were housed in standard conditions, and all the experiments were conducted in accordance with the "Guide for the Care and Use of Laboratory Animals" prepared by the Institutional Animal Care and Use Committee of National Taiwan University.

F344 rats were anesthetized with 2% isoflurane mixed oxygen. About $1 \times 10^6$ GP7TB rat liver epithelial tumour cells in 0.05 ml PBS were injected into a region in the middle lobe of liver and $2 \times 10^6$ GP7TB cell in 0.05 ml PBS were injected under the dorsal skin of rat. Tumours were allowed to develop for 4 weeks after inoculation then the rats were randomly divided into groups. The different groups of rats were injected with PBS control, TfR control (3 nmol), or TfR-CEBPA (3 nmol) via tail vein or subcutaneous route 3 times/week for 3 weeks. Tumour size on the back was recorded every week during the injection treatment. The rats were sacrificed two days after last injection by $CO_2$. Tumours on the back and in the liver were removed from rats. Tumours were weighed and tumour size was measured by ruler then stored at −80° C. for following analysis. Blood samples were collected from heart and were centrifuged at room temperature for 15 min at 3000 rpm and the serum were preserved at −80° C. until assayed.

Figure 6:
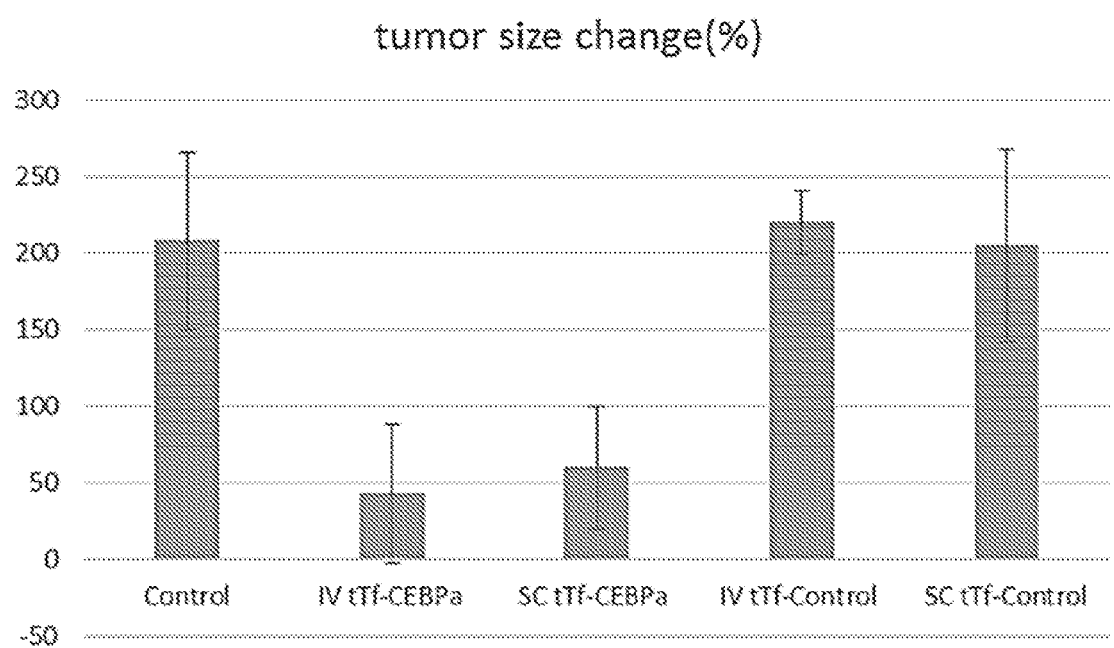
FIG. 6. Graph showing the percentage tumour size change in a hepatocellular carcinoma model in male F344 rats after intravenous (IV) or subcutaneous (SC) administration of TfR-CEBPA saRNA.

The results are shown in FIG. 6. TfR carrying CEBPA saRNA was able to reduce tumour growth compared to control treatment, whether TfR was administered intravenously or subcutaneously.

Metastatic Pancreatic Cancer Model in Mice

A firefly luciferase fragment was inserted into the pcDNA-3.1(+) backbone encoding ampicillin resistance for selection in bacteria and neomycin gene for selection in mammalian cells. The recombinant constructs for stable cell line were purified using plasmid midi kit (QIAGEN, USA). Panc-1 (human pancreatic carcinoma) cells were transfected with recombinant constructs for 24 h. The following day, culture medium was replaced with standard medium containing 1.2 mg/mL G418 (Merck, Germany) for stable clone selection. Two weeks after selection, a single stable cell line was picked and maintained in medium containing 1.2 mg/mL G418. Luciferase expression was assessed using the Luciferase Assay System.

To establish the traceable tumour animal models, subcutaneous implantations were performed by injecting 30 ul of a monocellular suspension in PBS containing $1 \times 10^6$ Panc-1 with luciferase expression (Panc-1-Luc) cells into a region in the middle lobe of liver of 6-week-old female NOD/SCID mice (BioLasco Co., Taiwan). Tumours were allowed to develop for 1 week after inoculation then the mice were randomly divided into 5 groups and injected with PBS, TfR-CEBPA (1 nmol), control TfR-CEBPA (1 nmol), P19-CEBPA (1 nmol) or control P19-CEBPA (1 nmol) via tail vein 3 times/week for 3 weeks. The P19 aptamer is described in WO 2013/154735. The mice were sacrificed two days after last injection by $CO_2$. Tumours were removed from mice and tumour size was measured by ruler. Tumour growth was monitored by evaluating bioluminescence using the spectrum of IVIS 200 before first injection and one day after last injection.

Prior to the in vivo imaging, the mice were anesthetized using isoflurane. A solution of 150 µg/kg D-luciferin (Biosynth, USA) was then injected by the intraperitoneal route. The mice were imaged in the spectrum of IVIS 200 and bioluminescent signals were analysed using Living Image Software (Caliper Life Sciences, Alameda, Calif.).

Figure 7A:
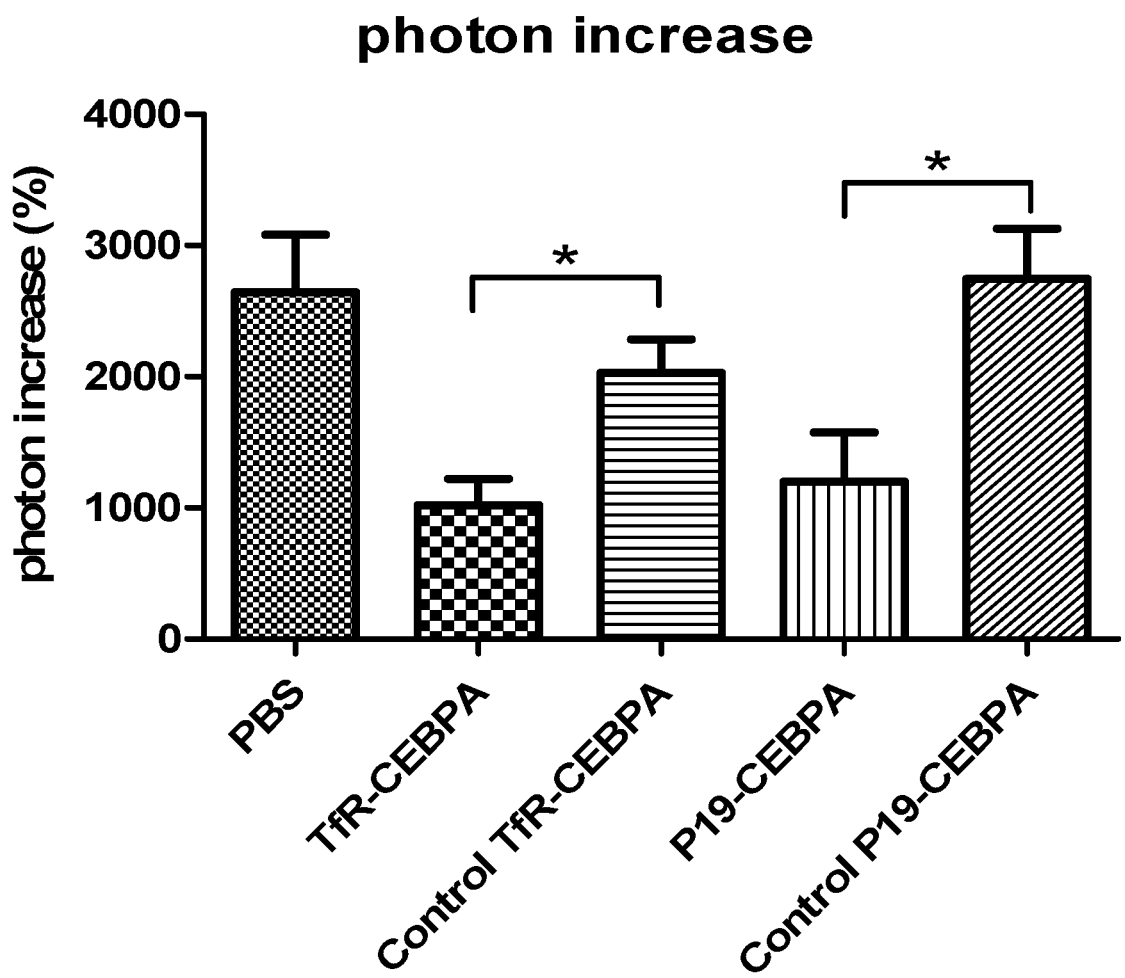
FIGS. 7A and 7B. Graphs showing the effect of TfR-CEBPA and P19-CEBPA treatment in a metastatic pancreatic cancer model in mice compared to aptamer controls.
Figure 7B:
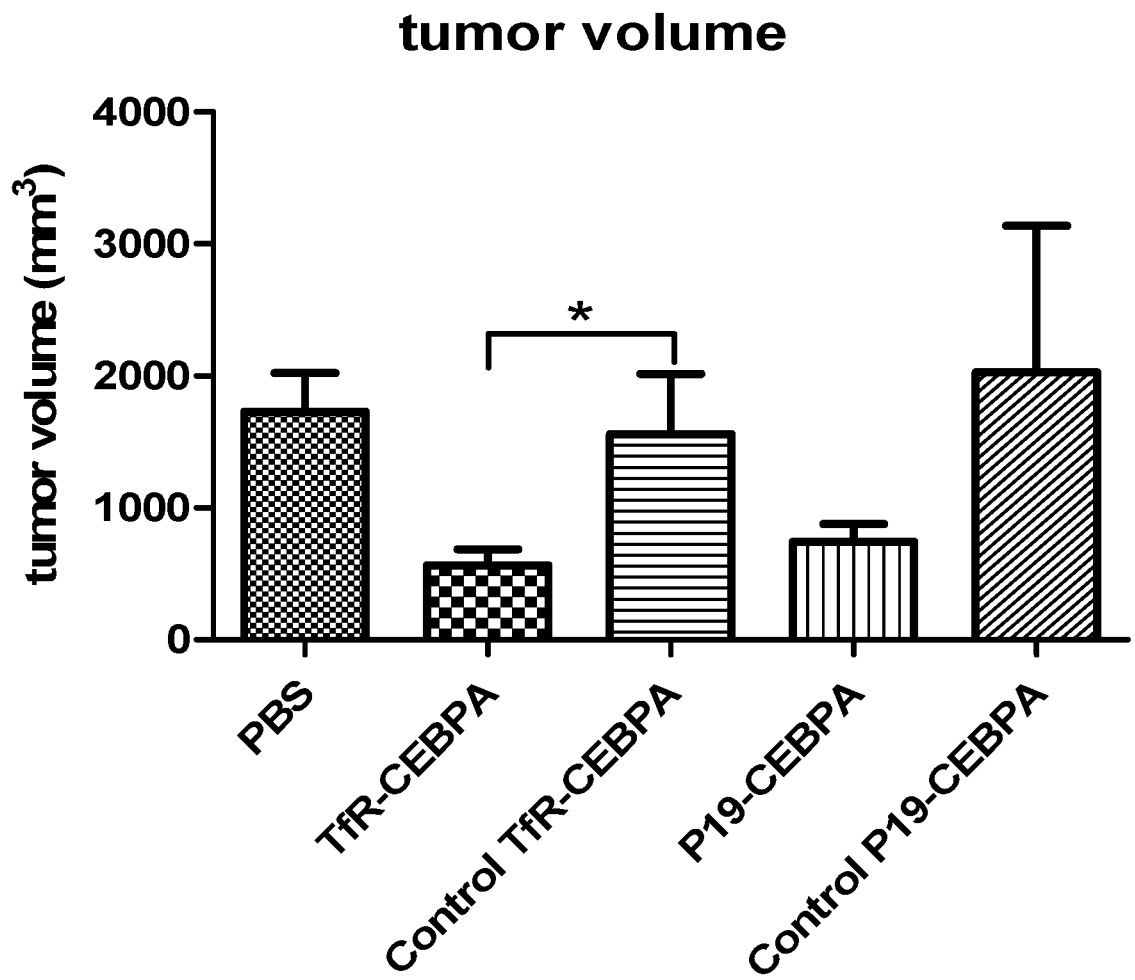
Figure 8A:
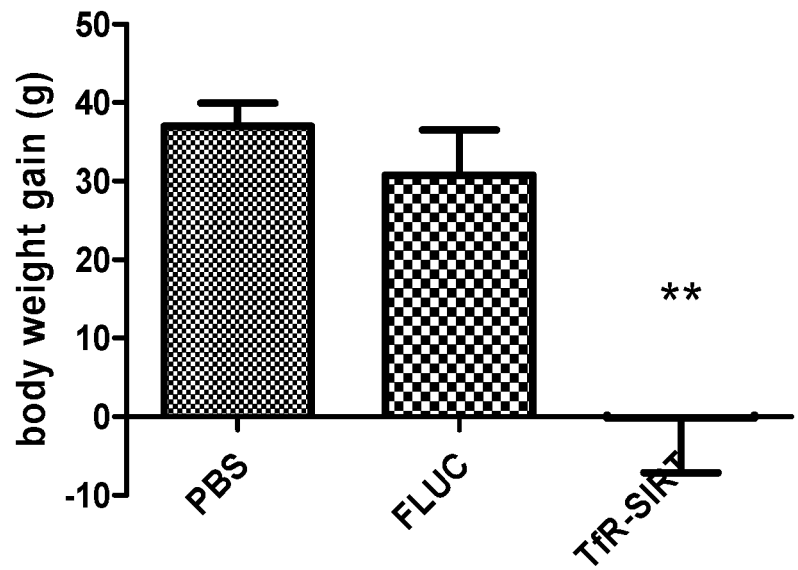
FIGS. 8A to 8F. Graphs showing ability of TfR-SIRT treatment to improve symptoms associated with metabolic diseases in F344 rats fed on a high-fat diet.
Figure 8B:
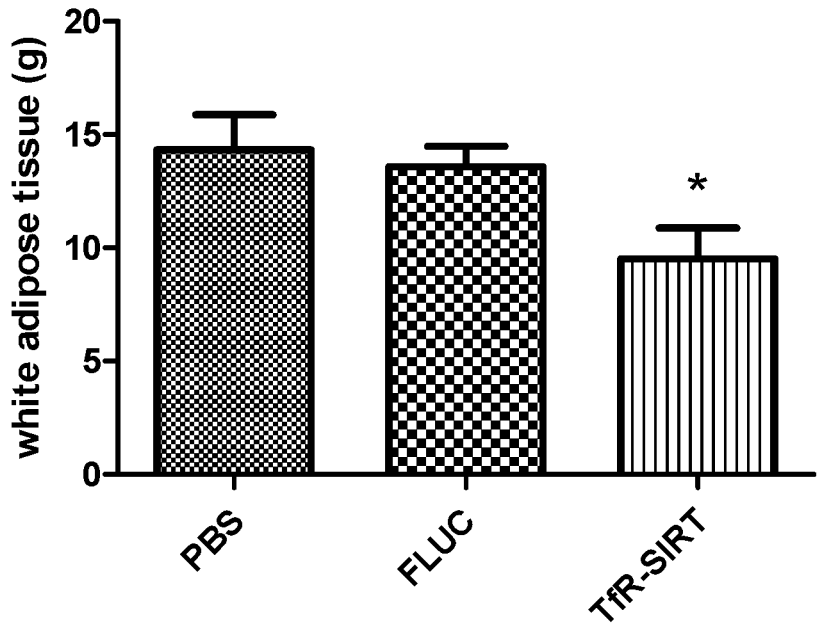
Figure 8C:
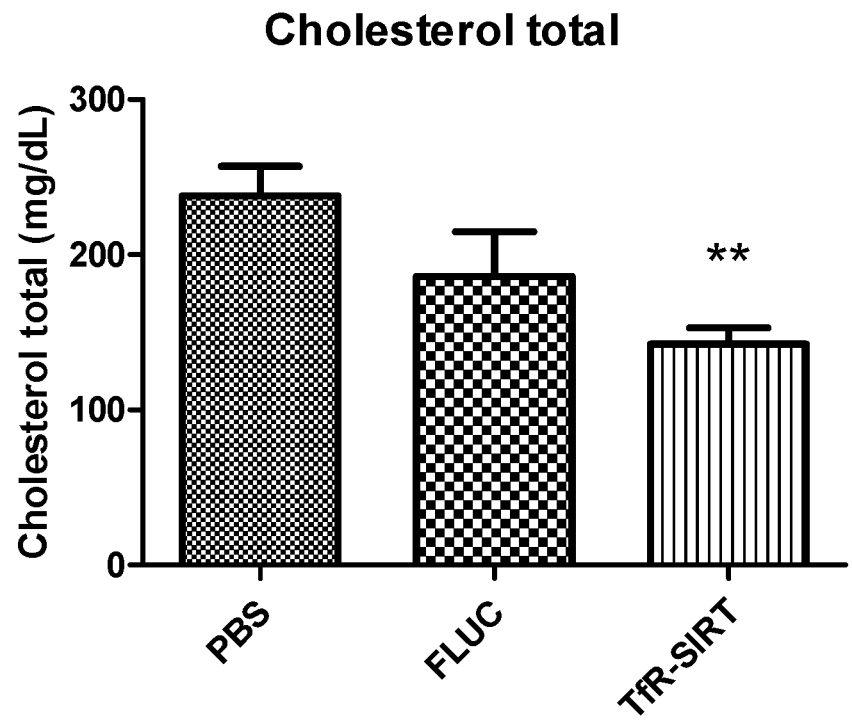
Figure 8D:
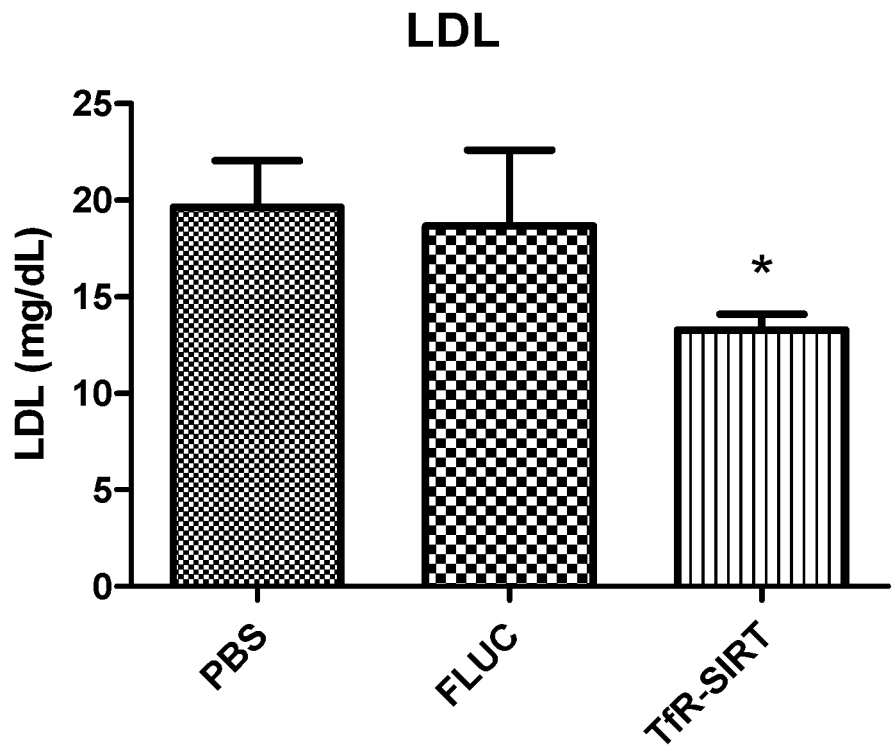
Figure 8E:
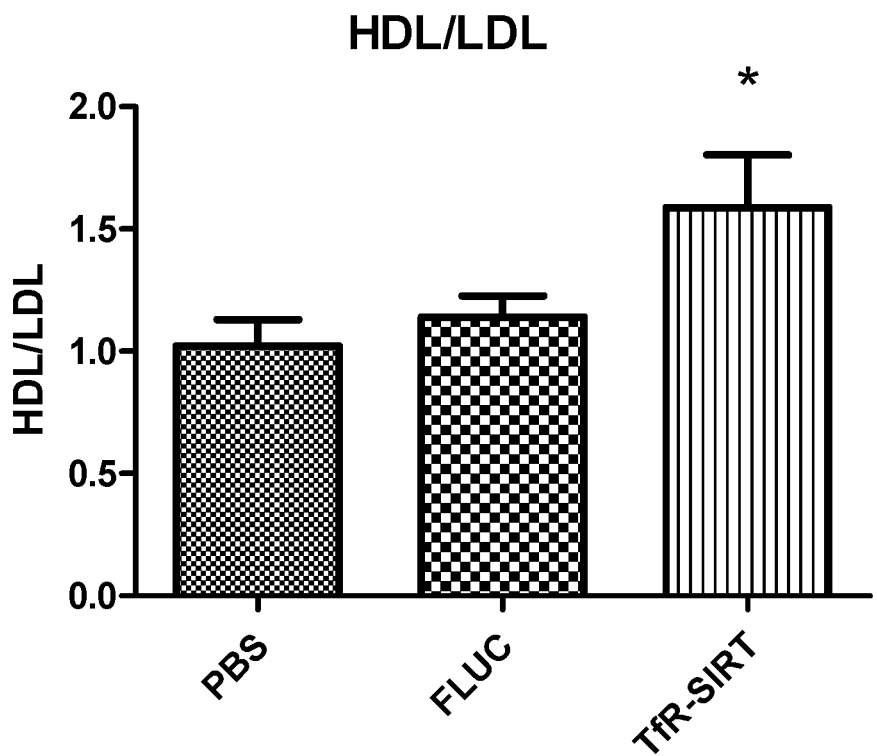
Figure 8F:
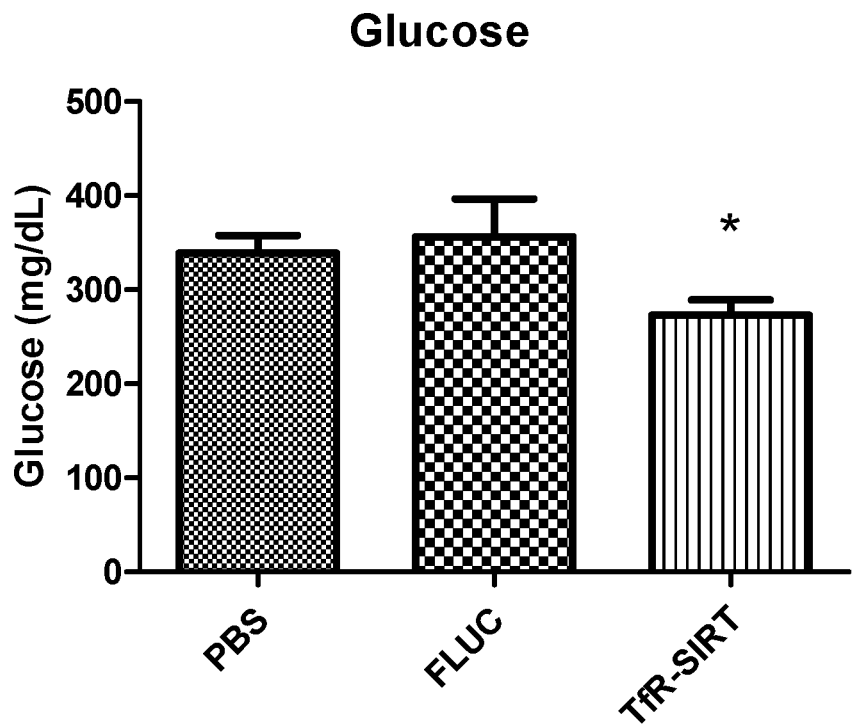

The results are shown in FIGS. 7A and 7B. Mice that were treated with TfR-CEBPA demonstrated significantly reduced tumour growth (7A; determined by reduced photon increase) and significantly reduced tumour volume (7B) compared with the control groups.

Example 5

TR14 S1-3 Aptamer Delivers Payloads In Vivo to Cells Related to Metabolic Diseases The ability of the TR14 S1-3 aptamer and SIRT1 saRNA to improve metabolic disorders was assessed.

A ribonucleic acid was synthesised comprising TR14 S1-3 (TfR; SEQ ID NO:1), five C3 (phosphoramidite) spacers and a SIRT1 saRNA. The sense and antisense sequences of the CEBPA saRNA are shown in SEQ ID NO:7 and SEQ ID NO:8, respectively. The sense and antisense sequences each comprise a 2-nucleotide (UU) overhang at the 3' end.

20 male F344 rats at 10 weeks of age were obtained from BioLASCO Taiwan Co., Ltd. The rats were housed in standard conditions, and all the experiments were conducted in accordance with the "Guide for the Care and Use of Laboratory Animals" prepared by the Institutional Animal Care and Use Committee of National Taiwan University.

After 1 week of acclimatization, the rats were fed a high fat diet: 88% standard laboratory diet, 10% lard oil (Merck KGaA, Darmstadt, Germany) and 2% cholesterol ((Merck KGaA, Darmstadt, Germany) for 26 weeks. After 14 weeks high fat feeding, the rats were separated into groups (5 rats in each group). The rats in four groups were injected with PBS, FLUC, and TfR-SIRT1 respectively 1 time/week via tail vein for 12 weeks. At the end of the experiment, the animals were fasted overnight and then sacrificed by $CO_2$. Livers, brain, brown fat and white fat harvested from rats were weighed then stored at −80° C. Blood samples collected in centrifuge tubes were centrifuged at 3000 rpm for 15 minutes. Serum was stored at −80° C. until used for biochemical assays.

Body weight was recorded every week during the injection treatment. The complete blood count (CBC) test is performed by hematology analyzer Sysmex HST-N402XE (Sysmex, Japan). The serum levels of glucose, total cholesterol, high density lipoprotein (HDL) cholesterol and low density lipoprotein (LDL) cholesterol were measured with VITROS 5,1 FS Chemistry System (Ortho Clinical Diagnostics, USA).

After the rats were sacrificed, livers and brains were immediately removed then fixed in 4% (w/v) paraformaldehyde. Then, the livers and brains were embedded in paraffin and sections (of 4 μm thickness) were sliced then stained with H&E.

To measure cholesterol, 10 mg liver tissue was extracted with 200 μl of chloroform:Isopropanol:NP-40 (7:11:0.1) in a micro-homogenizer. The extract was centrifuged for 5-10 minutes at 15,000 g. The liquid (organic phase) was transferred to a new tube and air dried at 50° C. to remove chloroform. The samples were put under vacuum for 30 min to remove trace organic solvent. Cholesterol extracted from liver was quantified enzymatically using a Cholesterol/Cholesteryl Ester Quantitation Kit (K603-100; Biovision) following the manufacturer's instructions.

The results are shown in FIGS. 8A to 8F. Rats on a high fat diet and treated with TfR-SIRT1 did not gain weight (8A). The same rats also showed decreased levels of white adipose tissue (8B), total cholesterol (8C), LDL (8D), and fasting blood glucose (8F). In addition, the rats demonstrated an increased HDL/LDL ratio (8E), thus indicating a higher level of HDL ("good" cholesterol) compared to LDL ("bad" cholesterol). All results indicate that treatment with TfR-SIRT1 is able to ameliorate metabolic disorders, and that intravenously-administered TfR is able to deliver a payload to tissues in which it is required.

The invention claimed is:

1. A ribonucleic acid compound comprising, or consisting of, an RNA sequence having at least 90% sequence identity to SEQ ID NO:1, wherein said ribonucleic acid compound has a length of 29 nucleotides or fewer, and wherein the ribonucleic acid compound is capable of binding to a transferrin receptor (TfR).

2. The ribonucleic acid compound according to claim 1, wherein said ribonucleic acid compound has a length of 22 nucleotides or fewer.

3. The ribonucleic acid compound according to claim 1, wherein the RNA sequence has 100% sequence identity to SEQ ID NO:1.

4. A ribonucleic acid compound comprising, or consisting of, an RNA sequence having at least 90% sequence identity to SEQ ID NO:5, wherein said ribonucleic acid compound has a length of 29 nucleotides or fewer, and wherein the ribonucleic acid compound is capable of binding to a transferrin receptor (TfR).

5. The ribonucleic acid compound according to claim 4, wherein said ribonucleic acid compound is 16 nucleotides in length.

6. The ribonucleic acid compound according to claim 4, wherein the RNA sequence has 100% sequence identity to SEQ ID NO:5.

7. The ribonucleic acid compound according to claim 1, wherein the ribonucleic acid compound is capable of binding to TfR on a cell surface.

8. The ribonucleic acid compound according to claim 1, which is capable of being internalised into a cell.

9. The ribonucleic acid compound according to claim 1, which is capable of traversing the blood-brain barrier.

10. The ribonucleic acid compound according to claim 1, further comprising a compound moiety attached to said RNA sequence.

11. The ribonucleic acid compound according to claim 10, wherein: (a) the compound moiety is a therapeutic moiety or an imaging moiety; or (b) said compound moiety is covalently attached to said RNA sequence.

12. The ribonucleic acid compound according to claim 11, wherein:
(a) said therapeutic moiety is a nucleic acid moiety, a peptide moiety or a small molecule drug moiety;
(b) said therapeutic moiety is an activating nucleic acid moiety or an antisense nucleic acid moiety;
(c) said therapeutic moiety is a miRNA, mRNA, saRNA or siRNA moiety;
(d) said therapeutic moiety is an anticancer therapeutic moiety;
(e) said therapeutic moiety is a C/EBPalpha saRNA moiety, a SIRT1 saRNA moiety, or a HNF saRNA moiety; or
(f) the imaging moiety is a bioluminescent molecule, a photoactive molecule, a metal or a nanoparticle.

13. A pharmaceutical composition comprising a ribonucleic acid compound according to claim 1, optionally comprising a pharmaceutically acceptable excipient.

14. The pharmaceutical composition according to claim 13, further comprising a therapeutic agent, optionally an anticancer agent.

15. A method of delivering a compound into a cell, the method comprising:
(i) contacting a cell with a compound and the ribonucleic acid compound according to claim 1; and
(ii) allowing said ribonucleic acid compound to bind to a transferrin receptor on said cell and pass into said cell thereby delivering said compound into said cell.

16. The method according to claim 15, wherein said compound is a therapeutic agent or an imaging agent.

17. A method of treating or preventing a disease or disorder in a subject in need thereof, the method comprising administering to the subject an effective amount of a ribonucleic acid compound according to claim 1.

18. The method according to claim 17, wherein the disease or disorder is cancer.

19. The method according to claim 18, wherein the method further comprises administering an anticancer agent.

20. The method according to claim 17, wherein the disease or disorder is a metabolic disorder or a neurological disorder.

21. A method of detecting a cell, the method comprising:
(i) contacting a cell with the ribonucleic acid compound according to claim 1, wherein the ribonucleic acid compound comprises an imaging moiety;
(ii) allowing said ribonucleic acid compound to bind to a transferrin receptor on said cell and pass into said cell; and
(iii) detecting said imaging moiety thereby detecting said cell.

* * * * *